US009266827B2

(12) United States Patent
Aicher et al.

(10) Patent No.: US 9,266,827 B2
(45) Date of Patent: Feb. 23, 2016

(54) BICYCLIC SULFONE COMPOUNDS FOR INHIBITION OF RORGAMMA ACTIVITY AND THE TREATMENT OF DISEASE

(71) Applicants: Merck Sharp & Dohme Corp., Rahway, NJ (US); Lycera Corporation, Ann Arbor, MI (US)

(72) Inventors: Thomas D. Aicher, Ann Arbor, MI (US); Kenneth Jay Barr, Boston, MA (US); Vladimir Simov, South Boston, MA (US); William D. Thomas, San Jose, CA (US); Peter L. Toogood, Ann Arbor, MI (US); Chad A. Van Huis, Hartland, MI (US)

(73) Assignees: Merck Sharp & Dohme Corp., Rahway, NJ (US); Lycera Corporation, Ann Arbor, MI (US)

( * ) Notice: Subject to any disclaimer, the term of this patent is extended or adjusted under 35 U.S.C. 154(b) by 0 days.

(21) Appl. No.: 14/398,068

(22) PCT Filed: May 3, 2013

(86) PCT No.: PCT/US2013/039422
§ 371 (c)(1),
(2) Date: Oct. 30, 2014

(87) PCT Pub. No.: WO2013/069588
PCT Pub. Date: Nov. 14, 2013

(65) Prior Publication Data
US 2015/0126493 A1 May 7, 2015

Related U.S. Application Data

(60) Provisional application No. 61/644,143, filed on May 8, 2012.

(51) Int. Cl.
| | |
|---|---|
| C07D 233/72 | (2006.01) |
| C07D 263/22 | (2006.01) |
| C07D 207/12 | (2006.01) |
| C07C 317/40 | (2006.01) |
| A61K 31/10 | (2006.01) |
| A61K 31/16 | (2006.01) |
| A61K 31/47 | (2006.01) |
| C07C 311/30 | (2006.01) |
| C07D 263/44 | (2006.01) |
| C07D 207/27 | (2006.01) |
| C07D 209/52 | (2006.01) |
| C07D 211/96 | (2006.01) |
| C07D 213/82 | (2006.01) |
| C07D 215/38 | (2006.01) |
| C07D 217/22 | (2006.01) |
| C07D 223/16 | (2006.01) |
| C07D 231/18 | (2006.01) |
| C07D 401/12 | (2006.01) |
| C07D 471/04 | (2006.01) |
| C07D 491/052 | (2006.01) |

(52) U.S. Cl.
CPC ............ *C07C 317/40* (2013.01); *C07C 311/30* (2013.01); *C07D 207/12* (2013.01); *C07D 207/27* (2013.01); *C07D 209/52* (2013.01); *C07D 211/96* (2013.01); *C07D 213/82* (2013.01); *C07D 215/38* (2013.01); *C07D 217/22* (2013.01); *C07D 223/16* (2013.01); *C07D 231/18* (2013.01); *C07D 233/72* (2013.01); *C07D 263/22* (2013.01); *C07D 263/44* (2013.01); *C07D 401/12* (2013.01); *C07D 471/04* (2013.01); *C07D 491/052* (2013.01); *C07C 2101/02* (2013.01); *C07C 2101/14* (2013.01); *C07C 2102/00* (2013.01); *C07C 2102/10* (2013.01); *C07C 2102/22* (2013.01); *C07C 2102/42* (2013.01)

(58) Field of Classification Search
None
See application file for complete search history.

(56) References Cited

U.S. PATENT DOCUMENTS

| | | |
|---|---|---|
| 2007/0049556 A1 | 3/2007 | Zhang et al. |
| 2008/0153805 A1 | 6/2008 | Ceccarelli et al. |

FOREIGN PATENT DOCUMENTS

| | | |
|---|---|---|
| JP | H06250441 A | 9/1994 |
| WO | WO-2010/017827 A1 | 2/2010 |

OTHER PUBLICATIONS

André et al., "Disruption of retinoid-related orphan receptor β changes circadian behaviour, causes retinal degeneration and leads to *vacillans* phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Berge et al., "Pharmaceutical salts," 66(1) J. Pharm. Sci. 1-19 (1977).
Carlberg et al., "RZRs, a new family of retinoid-related orphan receptors that function as both monomers and homodimers," 8 Mol. Endocrinol. 757-70 (1994).
Dussault et al., "Orphan nuclear receptor RORα-deficient mice display the cerebellar defects of *staggerer*," 70 Mech. Develop. 147-53 (1998).
Gennaro (ed.), *Remington: The Science and Practice of Pharmacy*, 20th edition (2000).
Giguère et al., "Isoform-specific amino-terminal domains dictate DNA-binding properties of RORα, a novel family of orphan hormone nuclear receptors," 8 Genes & Develop. 538-53 (1994).

(Continued)

*Primary Examiner* — Zinna Northington Davis
(74) *Attorney, Agent, or Firm* — Goodwin Procter LLP

(57) ABSTRACT

The invention provides bicyclic sulfone compounds, pharmaceutical compositions, methods of inhibiting RORγ activity, reducing the amount of iL-17 in a subject, and treating immune disorders and inflammatory disorders using such bicyclic sulfone compounds. Another aspect of the invention provides a method of treating a subject suffering from a medical disorder. The method comprises administering to the subject a therapeutically effective amount of one or more bicyclic sulfone compounds described herein. In certain other embodiments, the disorder is rheumatoid arthritis.

52 Claims, No Drawings

(56) References Cited

OTHER PUBLICATIONS

Gould, "Salt selection for basic drugs," 33 Int'l J. Pharmaceutics 201-217 (1986).

Greene & Wuts, *Protective Groups in Organic Synthesis*, 2d Edition (1991).

Hanessian et al., "A versatile protocol for the stereocontrolled elaboration of vicinal secondary and tertiary centers of relevance to natural product synthesis," 52(6) J. Org. Chem. 1170-72 (1987).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Medvedev et al., "Cloning of a cDNA encoding the murine orphan receptor RZR/RORγ and characterization of its response element," 181 Gene 199-206 (1996).

Ortiz et al., "TOR: a new orphan receptor expressed in the thymus that can modulate retinoid and thyroid hormone signals," 9 Mol. Endocrinol. 1679-91 (1995).

Takano et al., "A new synthesis of a steroid side chain via stereocontrolled protonation: synthesis of (−)-desmosterol," 14 J. Chem. Soc., Chem. Commun. 760-61 (1983).

van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).

Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).

Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).

BICYCLIC SULFONE COMPOUNDS FOR INHIBITION OF RORGAMMA ACTIVITY AND THE TREATMENT OF DISEASE

CROSS REFERENCE TO RELATED APPLICATIONS

This application is a national stage of International (PCT) Patent Application Serial No. PCT/US2013/039422, filed May 3, 2013, which claims the benefit of and priority to U.S. Provisional Patent Application Ser. No. 61/644,143, filed May 8, 2012.

FIELD OF THE INVENTION

The invention provides bicyclic sulfone compounds, methods of inhibiting RORγ activity and/or reducing the amount of IL-17 in a subject, and therapeutic uses of the bicyclic sulfone compounds. For instance, one aspect of the present invention provides aromatic sulfone compounds, methods of using such compounds to inhibit RORγ activity and/or reduce the amount of IL-17 in a subject, and treat immune disorders and inflammatory disorders.

BACKGROUND OF THE INVENTION

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; Wiesenberg et al. in *Nucleic Acids Res.* (1995) vol. 23, 327-333; Carlberg et al. in *Mol. Endocrinol.* (1994) vol. 8, 757-770; and Becker-Andre et al. in *Biochem. Biophys. Res. Commun.* (1993) vol. 194, 1371-1379. Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-1080. RORγt plays a critical role in regulating differentiation of Th17 cells, a subset of T helper lymphocytes. A number of inflammatory cytokines, such as IL-17, IL-22, and IL-23, are synthesized in Th17 cells. These cytokines are important pathogenic factors for many immune and inflammatory diseases. Compounds capable of modulating RORγt activity are contemplated to provide a therapeutic benefit in the treatment of multiple medical disorders, including immune and inflammatory disorders.

Numerous immune and inflammatory disorders continue to afflict millions of patients worldwide. Significant advances have been made in treating these disorders. However, current therapies do not provide satisfactory results for all patients due to, for example, detrimental side effects or insufficient efficacy. Treatments for immune and inflammatory disorders vary depending on the particular medical disorder, and often involve use of immunosuppressive drugs. Surgery (e.g., splenectomy), plasmapheresis, or radiation can be used in certain instances.

One exemplary immune disorder in need of better therapy is psoriasis. Psoriasis is a T cell-mediated inflammatory disease that affects approximately 2% to 3% of adults and has a substantial adverse impact on the quality of life for patients suffering from this disorder. Plaques resulting from psoriasis can be painful and are visually unappealing. Various therapeutics have been developed in an attempt to treat psoriasis. However, the traditional therapies for psoriasis often have toxic adverse effects.

An exemplary inflammatory disorder in need of better treatment is rheumatoid arthritis. This form of arthritis is characterized by inflammation in the synovial membrane and results in destruction of bone. Numerous therapeutics have been developed in an attempt to treat this disorder. Exemplary therapeutics for treating rheumatoid arthritis include glucocorticoids, methotrexate, hydroxychloroquine, sulfasalazine, and leflunomide. However, current therapies are not effective for all patients. Moreover, some patients develop resistance to current therapies.

Accordingly, a need exists for improved treatments for immune disorders and inflammatory disorders. The present invention addresses this need and provides other related advantages.

SUMMARY

The invention provides bicyclic sulfone compounds, pharmaceutical compositions, methods of inhibiting RORγ activity and/or reducing the amount of IL-17 in a subject, and methods of treating various medical disorders using such compounds. In particular, one aspect of the invention provides a collection of bicyclic sulfone compounds represented by Formula I:

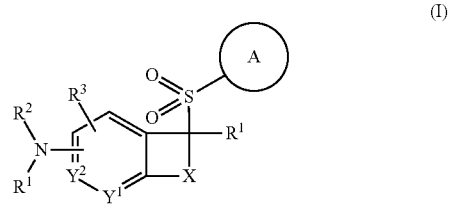

or a pharmaceutically acceptable salt or solvate thereof; wherein the variables are as defined in the detailed description. Further description of additional collections of bicyclic sulfone compounds, such as Formulae II-IV, are described in the detailed description.

Another aspect of the invention provides a method of treating a subject suffering from a medical disorder. The method comprises administering to the subject a therapeutically effective amount of one or more bicyclic sulfone compounds described herein, e.g., a compound of Formula I, II, III, or IV, wherein Formulae I-IV are as described in the detailed description. A large number of disorders can be treated using the bicyclic sulfone compounds described herein. For example, the compounds described herein can be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein. In certain other embodiments, the disorder is rheumatoid arthritis.

Another aspect of the invention provides a method of inhibiting the activity of RORγ. The method comprises exposing a RORγ to an effective amount of one or more bicyclic sulfone compounds described herein, e.g., a compound of Formula I, II, III, or IV, or a pharmaceutical composition described herein.

Another aspect of the invention provides a method of reducing the amount of IL-17 in a subject. The method comprises administering to a subject an effective amount of one or more bicyclic sulfone compounds described herein, e.g., a compound of Formula I, II, III, or IV, or a pharmaceutical composition described herein, to reduce the amount of IL-17 in the subject.

DETAILED DESCRIPTION OF THE INVENTION

The invention provides bicyclic sulfone compounds, pharmaceutical compositions, methods of inhibiting RORγ activity and/or reducing the amount of IL-17 in a subject, and therapeutic uses of the bicyclic sulfone compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and includes bicycloalkyls such as where two saturated carbocyclic rings are fused together. In certain embodiments, the cycloalkyls have about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The term "alkylene" refers to a diradical of an alkyl group. Exemplary alkylene groups include —$CH_2CH_2$—,

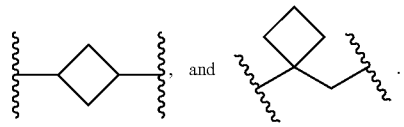

The term "cycloalkylene" refers to a diradical of a cycloalkyl group. Exemplary cycloalkylene groups include

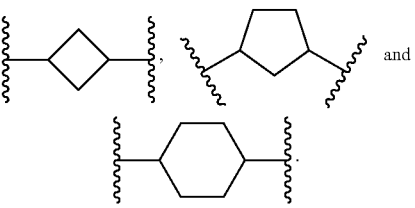

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl group. Exemplary hydroxyl alkyl groups include —$CH_2OH$, —$CH_2CH_2OH$, —$C(H)(OH)C(OH)H_2$, and the like.

The term "aralkyl" refers to an alkyl group substituted with an aryl group. Exemplary aralkyl groups include

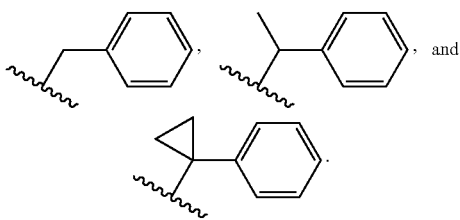

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more carbons are common to two adjoining rings (the rings are "fused rings") wherein all of the fused rings are heteroaromatic, e.g., in a naphthyridinyl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo [b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms.

The terms "amine" and "amino" are art-recognized and refer to both unsubstituted and substituted amines, e.g., a moiety that may be represented by the general formulas:

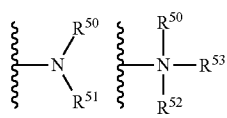

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—$R^{61}$, where m and $R^{61}$ are described above.

The term "oxo" is art-recognized and refers to a "═O" substituent. For example, a cyclopentane substituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the *IUPAC* 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required for 50% maximal effect.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection* and Use. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

The term "SEA Syndrome" refers to Seronegativity, Enthesopathy, Arthropathy Syndrome.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran.

The abbreviation "DCM" is art-recognized and refers to dichloromethane.

As a general matter, compositions specifying a percentage are by weight unless otherwise specified.

I. Bicyclic Sulfone Compounds

One aspect of the invention provides a compound represented by Formula I:

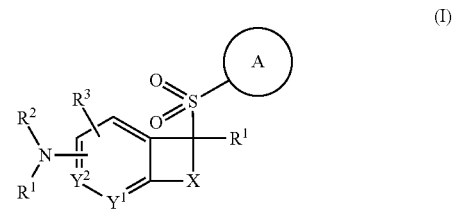

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p$$C_{1-6}$alkyl, —SO$_2$N($R^4$)($R^5$), —N($R^4$)SO$_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$—[C($R^6$)($R^7$)]—[C($R^6$)$_2$]$_m$-ψ, —C(O)—[C($R^6$)($R^7$)]—[C($R^6$)$_2$]$_m$-ψ, or —C($R^6$)$_2$—N($R^8$)—[C($R^6$)($R^7$)]—[C($R^6$)$_2$]$_m$-ψ; wherein ψ is a bond to the ring carbon atom bearing the sulfonyl in Formula I;

$Y^1$ and $Y^2$ are each independently C($R^3$) or N;

$R^1$ represents independently for each occurrence hydrogen or $C_{1-6}$alkyl;

$R^2$ is —C(O)-aryl, —C(O)-aralkyl, —C(O)—[C($R^6$)$_2$]$_m$ cycloalkyl, —C(O)—[C($R^6$)$_2$]$_m$— heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —SO$_2$N($R^4$)($R^5$), and —N($R^4$)SO$_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

R⁷ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)$ $(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O))N(R^4)$ $(R^5)$; or R⁷ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R⁸ is hydrogen, $C_{1-6}$alkyl, or —C(O)—$C_{1-6}$alkyl;

R⁹ is hydrogen, $C_{1-6}$alkyl, $C_{1-6}$hydroxyalkyl, $C_{1-6}$alkylene-$N(R^4)(R^5)$, or $C_{1-6}$alkylene-$N(R^4)C(O)$—$C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl.

In certain other embodiments, A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, X is —O—$[C(R^6)(R^7)]$—$[C(R^6)_2]_m$-ψ. In certain other embodiments, X is —$C(R^6)_2$—$[C(R^6)(R^7)]$—$[C(R^6)_2]_m$-ψ. In certain other embodiments, X is —C(O)—$[C(R^6)(R^7)]$—$[C(R^6)_2]_m$-ψ. In certain other embodiments, X is $C(R^6)_2$—$N(R^8)$—$[C(R^6)(R^7)]$—$[C(R^6)_2]_m$-ψ.

In certain embodiments, Y¹ and Y² are $C(R^3)$. In certain other embodiments, at least one of Y¹ and Y² is N. In certain other embodiments, Y¹ is N, and Y² is $C(R^3)$. In certain other embodiments, Y¹ is $C(R^3)$, and Y² is N. In certain other embodiments, Y¹ is N, and Y² is CH. In certain other embodiments, Y¹ is CH, and Y² is N.

In certain embodiments, R¹ is hydrogen.

In certain embodiments, R² is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R² is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R² is represented by:

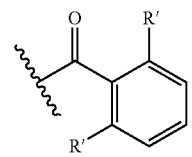

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, R² is represented by:

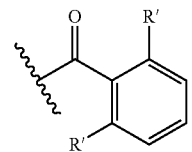

wherein each R' is independently halogen, $C_{1-6}$alkyl, or $C_{1-6}$haloalkyl.

In certain embodiments, R² is represented by:

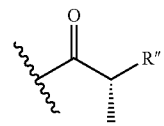

wherein R'' is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —$C(O)N(R^4)(R^5)$, —$S(O)_pC_{1-6}$alkyl, —$SO_2N(R^4)(R^5)$, and —$N(R^4)SO_2(C_{1-6}$alkyl). In certain embodiments, R'' is phenyl optionally substituted with 1, 2, or 3 substituents independently selected from the group consisting of halogen, $C_{1-6}$alkyl, and $C_{1-6}$haloalkyl.

In certain embodiments, R³ is hydrogen.

In certain embodiments, R⁷ is hydrogen. In certain other embodiments, R⁷ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)$ $(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, R⁷ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)$ ($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

In certain other embodiments, $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy.

Another aspect of the invention provides a compound represented by Formula I-A:

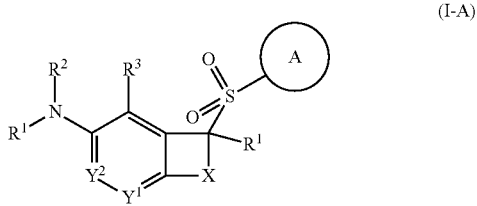

(I-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p$$C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$—[C($R^6$)($R^7$)]—[C($R^6$)$_2$]$_m$-ψ, —C(O)—[C($R^6$)($R^7$)]—[C($R^6$)$_2$]$_m$-ψ, or —C($R^6$)$_2$—N($R^8$)—[C($R^6$)($R^7$)]—[C($R^6$)$_2$]$_m$-ψ; wherein ψ is a bond to the ring carbon atom bearing the sulfonyl in Formula I-A;

$Y^1$ and $Y^2$ are each independently C($R^3$) or N;

$R^1$ represents independently for each occurrence hydrogen or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl; and m and p each represent independently for each occurrence 0, 1, or 2.

The definitions of variables in Formulae I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is aryl, and $R^2$ is —C(O)— aryl. Further, the definitions of variables A, X, $Y^1$, $Y^2$, $R^1$ to $R^9$, m, and p described in the preceding paragraphs in connection with Formula I are reiterated here for use in association with Formula I-A.

Another aspect of the invention provides a compound represented by Formula II:

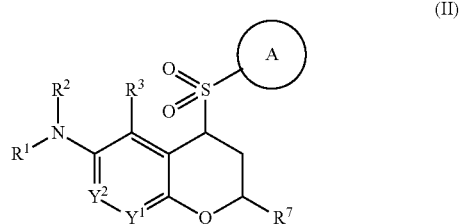

(II)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, and —$C_{1-4}$alkylene-N($R^4$)($R^5$);

$Y^1$ and $Y^2$ are each independently C($R^3$) or N;

$R^1$ is hydrogen or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or C$_{1-6}$alkylene-N(R$^4$)(C(O)N(R$^4$)(R$^5$); or R$^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, C$_{1-6}$alkyl, C$_{1-6}$haloalkyl, C$_{1-6}$hydroxyalkyl, C$_{1-6}$alkoxy, and C$_{1-6}$haloalkoxy;

R$^9$ is hydrogen, C$_{1-6}$alkyl, C$_{1-6}$hydroxyalkyl, C$_{1-6}$alkylene-N(R$^4$)(R$^5$), or C$_{1-6}$alkylene-N(R$^4$)C(O)—C$_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is aryl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is phenyl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is phenyl optionally substituted with 1, 2, or 3 substituents independently selected from the group consisting of halogen and C$_{1-6}$haloalkyl. In certain other embodiments, A is heterocycloalkyl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain embodiments, A is piperidine or pyrrolidine, each of which is optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy.

In certain embodiments, Y$^1$ and Y$^2$ are C(R$^3$). In certain other embodiments, at least one of Y$^1$ and Y$^2$ is N. In certain other embodiments, Y$^1$ is N, and Y$^2$ is C(R$^3$). In certain other embodiments, Y$^1$ is C(R$^3$), and Y$^2$ is N. In certain other embodiments, Y$^1$ is N, and Y$^2$ is CH. In certain other embodiments, Y$^1$ is CH, and Y$^2$ is N.

In certain embodiments, R$^1$ is hydrogen.

In certain embodiments, R$^2$ is —C(O)-aryl or —C(O)-aralkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, and C$_{1-6}$haloalkyl. In certain other embodiments, R$^2$ is —C(O)-aryl or —C(O)-aralkyl; each of which is substituted with 2 substituents independently selected from the group consisting of halogen, hydroxyl, C$_{1-6}$alkoxy, C$_{1-6}$haloalkoxy, C$_{1-6}$alkyl, and C$_{1-6}$haloalkyl, and said substituents are located at the ortho-positions of the aromatic ring. In certain other embodiments, R$^2$ is —C(O)-phenyl or —C(O)-benzyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, and C$_{1-6}$haloalkyl. In certain other embodiments, R$^2$ is —C(O)-phenyl or —C(O)-benzyl; each of which is optionally substituted with 1, 2, or 3 substituents independently selected from the group consisting of halogen, C$_{1-6}$alkyl, and C$_{1-6}$haloalkyl. In certain other embodiments, R$^2$ is represented by:

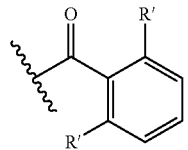

wherein each R' is independently halogen, hydroxyl, C$_{1-6}$alkoxy, C$_{1-6}$haloalkoxy, C$_{1-6}$alkyl, or C$_{1-6}$haloalkyl. In certain other embodiments, R$^2$ is represented by:

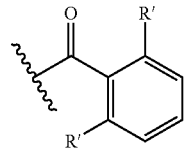

wherein each R' is independently halogen, C$_{1-6}$alkyl, or C$_{1-6}$haloalkyl.

In certain embodiments, R$^2$ is represented by:

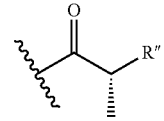

wherein R" is C$_{1-6}$alkyl, aryl, or heterocyclyl, each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl). In certain embodiments, R" is phenyl optionally substituted with 1, 2, or 3 substituents independently selected from the group consisting of halogen, C$_{1-6}$alkyl, and C$_{1-6}$haloalkyl.

In certain embodiments, R$^3$ is hydrogen.

In certain embodiments, R$^7$ is hydrogen. In certain other embodiments, R$^7$ is hydroxyl, C$_{1-6}$hydroxyalkyl, C$_{1-6}$alkyl, C$_{1-6}$haloalkyl, —CO$_2$R$^6$, C$_{1-6}$alkylene-CO$_2$R$^6$, C$_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or —N(R$^4$)C(O)R$^9$. In certain other embodiments, R$^7$ is C$_{1-6}$hydroxyalkyl, C$_{1-6}$alkyl, C$_{1-6}$alkylene-CO$_2$R$^6$, C$_{1-6}$alkylene-N(R$^4$)(R$^5$), or C$_{1-6}$alkylene-N(R$^4$)C(O)R$^9$. In certain other embodiments, R$^7$ is C$_{1-3}$hydroxyalkyl, methyl, ethyl, or C$_{1-3}$alkylene-N(H)C(O)—C$_{1-4}$alkyl.

Another aspect of the invention provides a compound represented by Formula III:

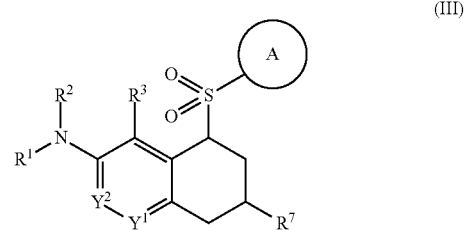

(III)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, and —C$_{1-4}$alkylene-N(R$^4$)(R$^5$);

Y$^1$ and Y$^2$ are each independently C(R$^3$) or N;

R$^1$ is hydrogen or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ represents independently for each occurrence hydrogen, halogen, or $C_{1-6}$alkyl;

R$^4$ and R$^5$ each represent independently for each occurrence hydrogen or $C_{1-6}$alkyl; or R$^4$ and R$^5$ taken together with the nitrogen atom to which they are attached form a 3-7 membered heterocyclic ring;

R$^6$ represents independently for each occurrence hydrogen or $C_{1-6}$alkyl;

R$^7$ is hydrogen, hydroxyl, $C_{1-6}$hydroxyalkyl, $C_{1-6}$alkyl, $C_{1-6}$haloalkyl, —CO$_2$R$^6$, $C_{1-6}$alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—C$_{1-6}$alkyl, or C$_{1-6}$alkylene-N(R$^4$)(C(O)N(R$^4$)(R$^5$); or R$^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R$^9$ is hydrogen, $C_{1-6}$alkyl, $C_{1-6}$hydroxyalkyl, $C_{1-6}$alkylene-N(R$^4$)(R$^5$), or $C_{1-6}$alkylene-N(R$^4$)C(O)—C$_{1-6}$alkyl;

n is 1 or 2; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy In certain embodiments, Y$^1$ and Y$^2$ are C(R$^3$). In certain other embodiments, at least one of Y$^1$ and Y$^2$ is N. In certain other embodiments, Y$^1$ is N, and Y$^2$ is C(R$^3$). In certain other embodiments, Y$^1$ is C(R$^3$), and Y$^2$ is N. In certain other embodiments, Y$^1$ is N, and Y$^2$ is CH. In certain other embodiments, Y$^1$ is CH, and Y$^2$ is N.

In certain embodiments, R$^1$ is hydrogen.

In certain embodiments, R$^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R$^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R$^2$ is represented by:

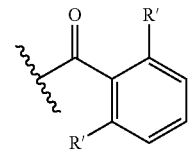

wherein each R' is independently halogen, $C_{1-6}$alkyl, or $C_{1-6}$haloalkyl. In certain other embodiments, R$^2$ is represented by:

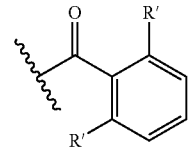

wherein each R' is independently halogen, hydroxyl, $C_{1-6}$alkoxy, $C_{1-6}$haloalkoxy, $C_{1-6}$alkyl, or $C_{1-6}$haloalkyl.

In certain embodiments, R$^2$ is represented by:

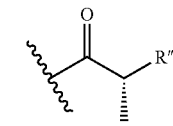

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, R$^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-N(H)C(O)—$C_{1-4}$alkyl.

Another aspect of the invention provides a compound represented by Formula IV:

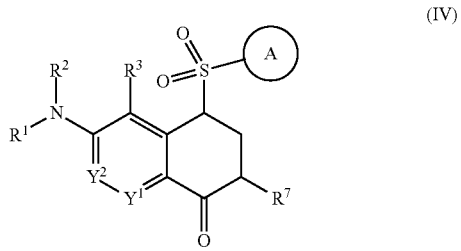

(IV)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

$Y^1$ and $Y^2$ are each independently $C(R^3)$ or N;

$R^1$ is hydrogen or $C_{1-6}$alkyl;

$R^2$ is —C(O)-aryl, —C(O)-aralkyl, —C(O)—$[C(R^6)_2]_m$-cycloalkyl, —C(O)—$[C(R^6)_2]_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)$N(R^4)(R^5)$, —$S(O)_pC_{1-6}$alkyl, —$SO_2N(R^4)(R^5)$, and —$N(R^4)SO_2(C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-6}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $C_{1-6}$alkylene-$N(R^4)(R^5)$, or $C_{1-6}$alkylene-$N(R^4)C(O)$—$C_{1-6}$alkyl;

n is 1 or 2; and m and p each represent independently for each occurrence 0, 1, or 2.

The definitions of variables in Formula IV above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is aryl, and $R^2$ is —C(O)— aryl. Further, the definitions of variables A, $Y^1$, $Y^2$, $R^1$ to $R^7$, $R^9$, m, and p described in the preceding paragraphs in connection with Formula III are reiterated here for use in association with Formula IV.

More generally, the definitions of variables in Formulae I through IV above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is one of the compounds listed in Tables 1-3 herein below, Table 4 in the Examples, or a pharmaceutically acceptable salt of any of the foregoing.

TABLE 1

| No. | Y | Z |
|---|---|---|
| I-1 | 2,6-disubstituted benzamide (Cl, CF3) | 4-fluorophenyl |
| I-2 | 2,6-disubstituted benzamide (F, CF3) | 3-chlorophenyl |
| I-3 | 2,6-disubstituted benzamide (CF3, CF3) | 3-cyclopropylphenyl |

TABLE 1-continued

| No. | Y | Z |
|---|---|---|
| I-4 | 2-Cl, 6-F benzamide | 4-F phenyl |
| I-5 | 2,6-diF benzamide | 3-Cl phenyl |
| I-6 | 2,6-diCl benzamide | 3-cyclopropyl phenyl |
| I-7 | (4-Cl phenyl)acetamide | 4-F phenyl |
| I-8 | pyridine-3-carboxamide | 3-Cl phenyl |
| I-9 | (S)-2-phenylpropanamide | 3-cyclopropyl phenyl |
| I-10 | cyclohexanecarboxamide | 4-F phenyl |
| I-11 | 2-Cl, 6-CF₃ benzamide | 3-CF₃ phenyl |
| I-12 | 2-F, 6-CF₃ benzamide | 3,4-diF phenyl |
| I-13 | 2-Cl, 6-CF₃ benzamide | 3-CF₃ phenyl |
| I-14 | 2-Cl, 6-F benzamide | 3,4-diF phenyl |
| I-15 | 2,6-diF benzamide | 3-CF₃ phenyl |
| I-16 | 2,6-diCl benzamide | 3,4-diF phenyl |
| I-17 | (4-Cl phenyl)acetamide | 3-CF₃ phenyl |

TABLE 1-continued

| No. | Y | Z |
|---|---|---|
| I-18 | nicotinamide | 3,4-difluorophenyl |
| I-19 | (R)-2-phenylpropanamide | 3-(trifluoromethyl)phenyl |
| I-20 | cyclohexanecarboxamide | 3,4-difluorophenyl |
| I-21 | 2-chloro-6-(trifluoromethyl)benzamide | 1-methyl-1H-pyrazol-4-yl |
| I-22 | 2-fluoro-6-(trifluoromethyl)benzamide | 1-methyl-1H-pyrazol-4-yl |
| I-23 | 2-chloro-6-(trifluoromethyl)benzamide | 5-fluoropyridin-2-yl |
| I-24 | 2-chloro-6-fluorobenzamide | 1-methylpiperidin-4-yl |
| I-25 | 2,6-difluorobenzamide | 1-methylpyrrolidin-3-yl |
| I-26 | (2,6-dichlorobenzyl)amino | 1H-pyrazol-1-yl |
| I-27 | 2-(4-chlorophenyl)acetamide | 1H-imidazol-1-yl |
| I-28 | nicotinamide | 5-fluoropyridin-2-yl |
| I-29 | (R)-2-phenylpropanamide | piperidin-1-yl |
| I-30 | cyclohexanecarboxamide | 1-methylpyrrolidin-3-yl |
| I-31 | isobutyramide | 3-methoxyphenyl |
| I-32 | isobutyramide | 4-fluorophenyl |

TABLE 1-continued

| No. | Y | Z |
|---|---|---|
| I-33 | isobutyramide | 3-chlorophenyl |
| I-34 | (S)-2-methoxypropanamide | 3-methoxyphenyl |
| I-35 | (R)-2-methoxypropanamide | 3-chlorophenyl |
| I-36 | cis-bicyclo[3.3.0]octyl propanamide | 3-chlorophenyl |
| I-37 | cis-bicyclo[3.3.0]octyl propanamide | 3-methoxyphenyl |
| I-38 | 2-chloro-6-(trifluoromethyl)benzamide | 3-methoxyphenyl |
| I-39 | 2-fluoro-6-(trifluoromethyl)benzamide | cis-octahydrocyclopenta[c]pyrrol-2-yl |
| I-40 | 2-chloro-6-(trifluoromethyl)benzamide | (2S,5R)-2-(hydroxymethyl)-5-methylpiperidin-1-yl |

TABLE 2

| No. | Y | A-B | Z |
|---|---|---|---|
| II-1 | 2-chloro-6-(trifluoromethyl)benzamide | 5,6,7,8-tetrahydroquinoline | 4-fluorophenyl |

TABLE 2-continued

| No. | Y | [A-B ring] | Z |
|---|---|---|---|
| II-2 | 2-F, 6-CF₃ benzamide | 5,6,7,8-tetrahydroquinoline (5-position) | 3-CF₃ phenyl |
| II-3 | 2,6-diF benzamide | 5,6,7,8-tetrahydroquinoline (5-position) | 3,4-diF phenyl |
| II-4 | 2-Cl, 6-F benzamide | 5,6,7,8-tetrahydroquinoline (5-position) | 1-methyl-1H-pyrazol-4-yl |
| II-5 | 2,6-diCl benzamide | 5,6,7,8-tetrahydroquinoline (5-position) | piperidin-1-yl |
| II-6 | 2-Cl, 6-CF₃ benzamide | 5,6,7,8-tetrahydroquinoline (5-position) | 1-methylpyrrolidin-3-yl |
| II-7 | 2-Cl, 6-CF₃ benzamide | 7-(hydroxymethyl)-5,6,7,8-tetrahydroquinoline (5-position) | 4-F phenyl |
| II-8 | 2-F, 6-CF₃ benzamide | 7-(hydroxymethyl)-5,6,7,8-tetrahydroquinoline (5-position) | 3-CF₃ phenyl |

TABLE 2-continued
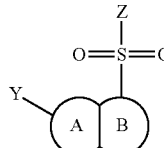
| No. | Y | | Z |
|---|---|---|---|
| II-9 | 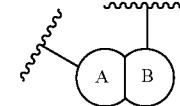 | 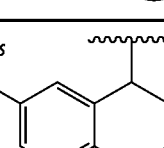 |  |
| II-10 | 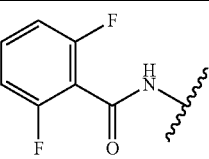 | 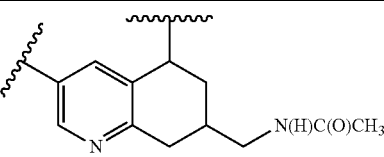 |  |
| II-11 | 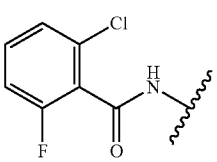 [SMILES: *NC(=O)c1c(F)cccc1Cl] | 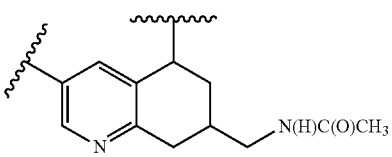 | 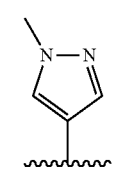 [SMILES: *c1cnn(C)c1] |
| II-12 | 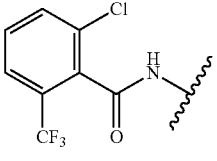 [SMILES: *NC(=O)c1c(Cl)cccc1C(F)(F)F] | 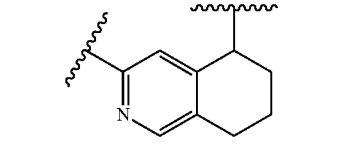 [SMILES: *c1cc2c(cn1)CCCC2*] | 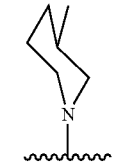 [SMILES: *N1CCCC(C)C1] |
| II-13 | 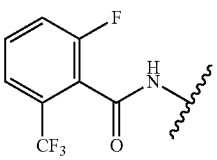 [SMILES: *NC(=O)c1c(F)cccc1C(F)(F)F] | 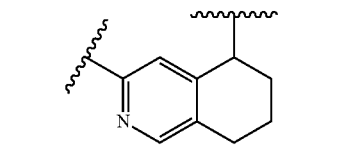 [SMILES: *c1cc2c(cn1)CCCC2*] | 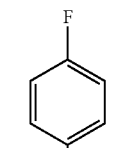 |
| II-14 | 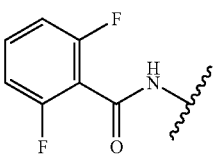 | 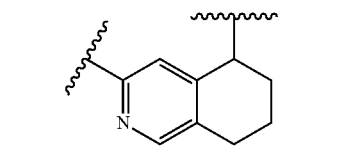 | 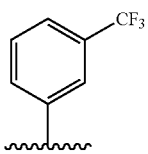 [SMILES: *c1cccc(C(F)(F)F)c1] |
| II-15 | 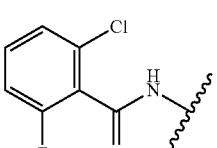 | 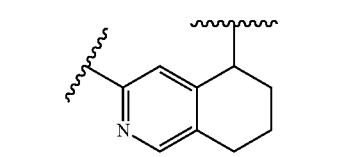 [SMILES: *c1cc2c(cn1)CCCC2*] | 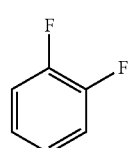 |

TABLE 2-continued
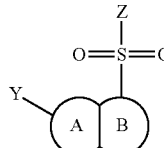
| No. | Y | | Z |
|---|---|---|---|
| II-16 | 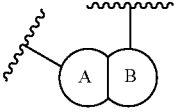 | 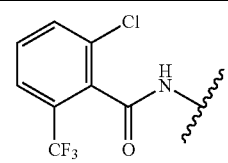 | 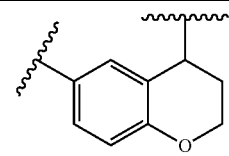 |
| II-17 | 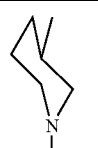 | 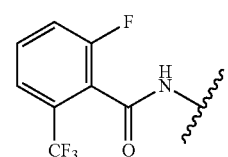 | 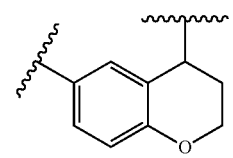 |
| II-18 | 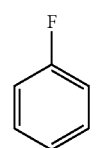 | 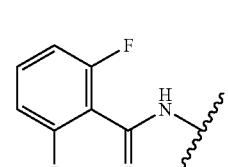 | 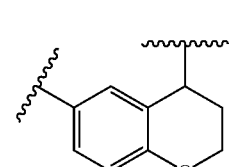 |
| II-19 | 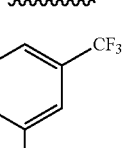 | 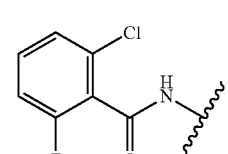 | 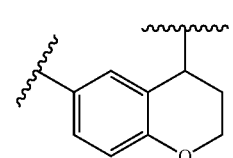 |
| II-20 | 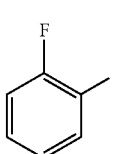 | 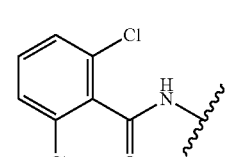 | 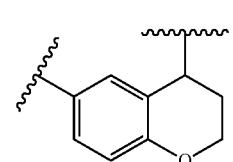 |
| II-21 | 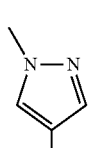 | 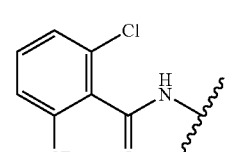 | 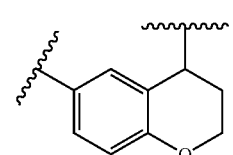 [SMILES: *c1cc2c(cn1)CCCC2*] |
| II-22 | 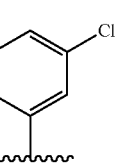 | 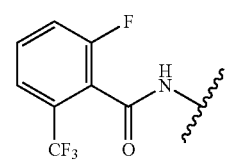 [SMILES: *NC(=O)c1c(Cl)cccc1C(F)(F)F] | 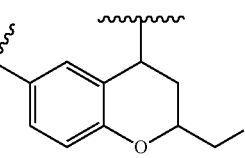 |

TABLE 2-continued

| No. | Y | | Z |
|---|---|---|---|
| II-23 | 2,6-difluorophenyl-C(O)NH- | chroman-4-yl with 6-linkage and 2-CH2OH | 3-(trifluoromethyl)phenyl |
| II-24 | 2-chloro-6-fluorophenyl-C(O)NH- | chroman-4-yl with 6-linkage and 2-CH2OH | 3,4-difluorophenyl |
| II-25 | 2,6-dichlorophenyl-C(O)NH- | chroman-4-yl with 6-linkage and 2-CH2N(H)C(O)CH3 | 1-methyl-1H-pyrazol-4-yl |
| II-26 | 2-chloro-6-(trifluoromethyl)phenyl-C(O)NH- | chroman-4-yl with 6-linkage and 2-CH2N(H)C(O)CH3 | piperidin-1-yl |
| II-27 | 2-fluoro-6-(trifluoromethyl)phenyl-C(O)NH- | chroman-4-yl with 6-linkage and 2-CH2N(H)C(O)CH3 | 4-fluorophenyl |
| II-28 | 2,6-difluorophenyl-C(O)NH- | 2-methylchroman-4-yl with 6-linkage | 3-(trifluoromethyl)phenyl |
| II-29 | 2-chloro-6-fluorophenyl-C(O)NH- | 2-methylchroman-4-yl with 6-linkage | 3,4-difluorophenyl |

TABLE 2-continued
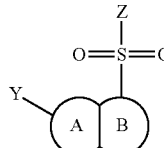
| No. | Y | | Z |
|---|---|---|---|
| II-30 | 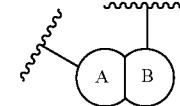 | 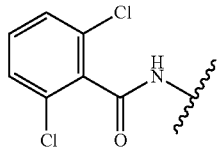 [SMILES: *NC(=O)c1c(Cl)cccc1Cl] | 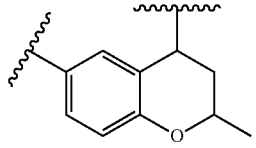 [SMILES: *c1ccc2c(c1)C(*)CC(C)O2] |
| II-31 | 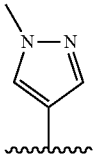 | 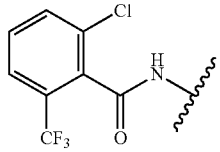 | 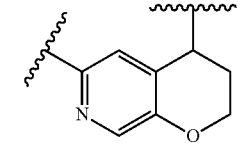 [SMILES: *c1cc2c(cn1)OCCC2*] |
| II-32 |  | 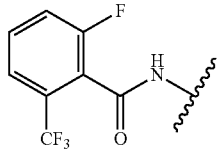 | 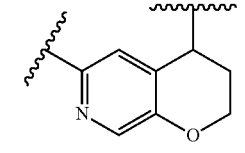 |
| II-33 | 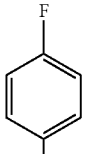 | 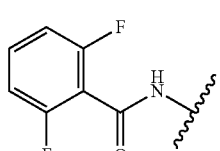 | 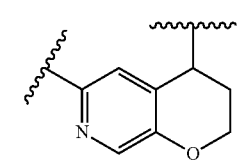 [SMILES: *c1cc2c(cn1)OCCC2*] |
| II-34 | 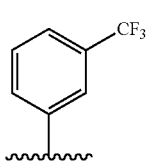 [SMILES: *c1cccc(C(F)(F)F)c1] | 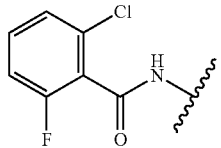 | 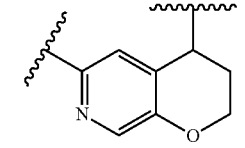 |
| II-35 |  | 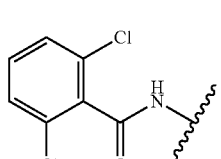 | 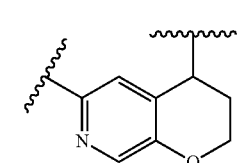 |
| II-36 | 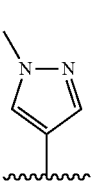 | 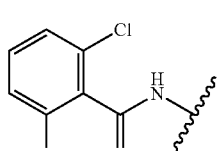 | 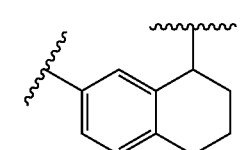 |

TABLE 2-continued

| No. | Y | | Z |
|---|---|---|---|
| II-37 | 2-F, 6-CF3 benzamide | 5-oxo-5,6,7,8-tetrahydronaphthalen-2-yl | 4-fluorophenyl |
| II-38 | 2,6-difluorobenzamide | 5-oxo-5,6,7,8-tetrahydronaphthalen-2-yl | 3-(trifluoromethyl)phenyl |
| II-39 | 2-Cl, 6-F benzamide | 5-oxo-5,6,7,8-tetrahydronaphthalen-2-yl | 3,4-difluorophenyl |
| II-40 | 2,6-dichlorobenzamide | 5-oxo-5,6,7,8-tetrahydronaphthalen-2-yl | 1-methyl-1H-pyrazol-4-yl |
| II-41 | 2-Cl, 6-CF3 benzamide | 8-oxo-5,6,7,8-tetrahydroisoquinolin-3-yl | piperidin-1-yl |
| II-42 | 2-F, 6-CF3 benzamide | 8-oxo-5,6,7,8-tetrahydroisoquinolin-3-yl | 4-fluorophenyl |

TABLE 2-continued

| No. | Y | | Z |
|---|---|---|---|
| II-43 | 2,6-difluorobenzamide | 3,4-dihydro-8(2H)-isoquinolinone (linked at 3- and 5-positions) | 3-(trifluoromethyl)phenyl |
| II-44 | 2-chloro-6-fluorobenzamide | 3,4-dihydro-8(2H)-isoquinolinone (linked at 3- and 5-positions) | 3,4-difluorophenyl |
| II-45 | 2,6-dichlorobenzamide | 2-methyl-2,3,4,5-tetrahydro-1H-2-benzazepine (linked at 7- and 5-positions) | 1-methyl-1H-pyrazol-4-yl |
| II-46 | 2-chloro-6-(trifluoromethyl)benzamide | 2-methyl-2,3,4,5-tetrahydro-1H-2-benzazepine (linked at 7- and 5-positions) | 3-chlorophenyl |
| II-47 | 2-fluoro-6-(trifluoromethyl)benzamide | 2-acetyl-2,3,4,5-tetrahydro-1H-2-benzazepine (linked at 7- and 5-positions) | 4-fluorophenyl |
| II-48 | 2,6-difluorobenzamide | 2-acetyl-2,3,4,5-tetrahydro-1H-2-benzazepine (linked at 7- and 5-positions) | 3-(trifluoromethyl)phenyl |

TABLE 2-continued
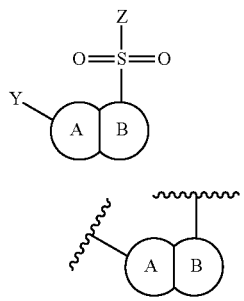
| No. | Y | | Z |
|---|---|---|---|
| II-49 | 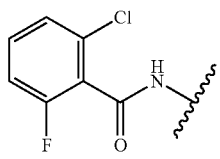 |  |  |
| II-50 | 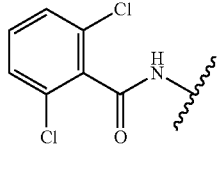 | 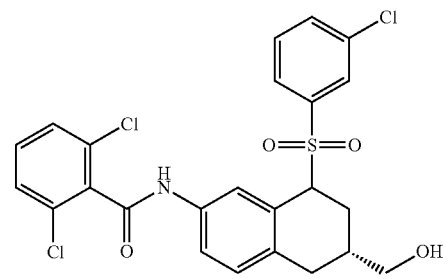 [SMILES: O=C(Nc1ccc2c(c1)C(S(=O)(=O)c1cccc(Cl)c1)C[C@H](CO)C2)c1c(F)cccc1Cl] | 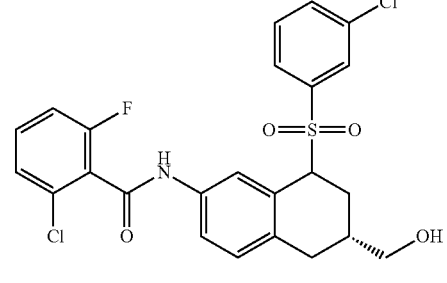 |
| TABLE 3 | | TABLE 3-continued | |
|---|---|---|---|
| No. | Compound | No. | Compound |
| III-1 | 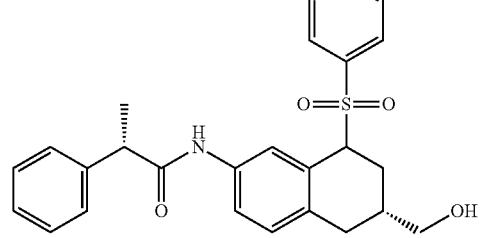 | III-4 | 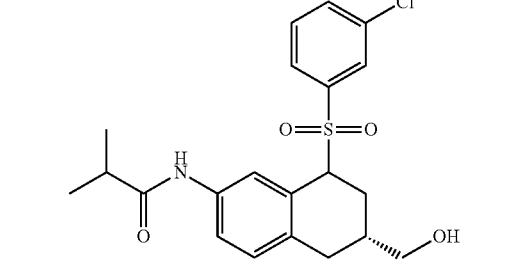 |
| III-2 | 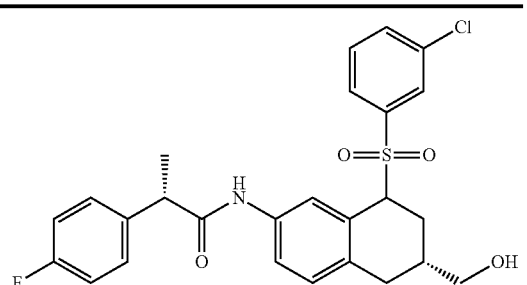 | III-5 | 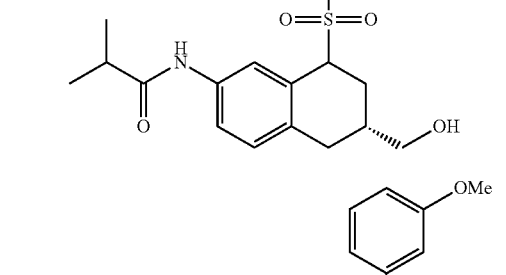 |
| III-3 | 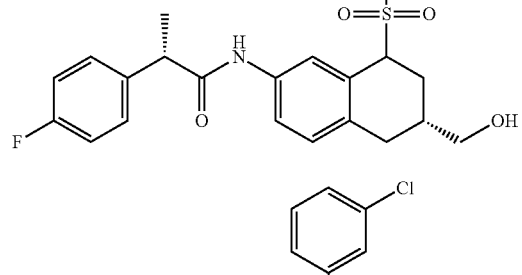 | III-6 | 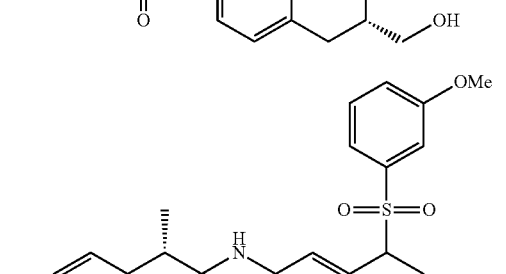 |

TABLE 3-continued

| No. | Compound |
|---|---|
| III-7 | (structure) |
| III-8 | (structure) |
| III-9 | (structure) |
| III-10 | (structure) |
| III-11 | (structure) |
| III-12 | (structure) |
| III-13 | (structure) |
| III-14 | (structure) |
| III-15 | (structure) |
| III-16 | (structure) |

TABLE 3-continued

| No. | Compound |
|---|---|
| III-17 | |
| III-18 | |
| III-19 | |
| III-20 | |
| III-21 | |
| III-22 | |
| III-23 | |
| III-24 | |
| III-25 | |

TABLE 3-continued
| No. | Compound |
|---|---|
| III-26 | 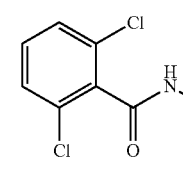 |
| III-27 | |
| III-28 | |
| III-29 | |
| III-30 | |
| III-31 | 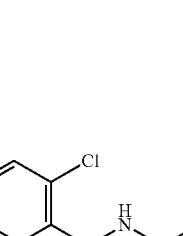 |
| III-32 | |
| III-33 | |
| III-34 | |
| III-35 | |

TABLE 3-continued

| No. | Compound |
|---|---|
| III-36 | (structure) |
| III-37 | (structure) |
| III-38 | (structure) |
| III-39 | (structure) |
| III-40 | (structure) |
| III-41 | (structure) |
| III-42 | (structure) |
| III-43 | (structure) |
| III-44 | (structure) |
| III-45 | (structure) |

TABLE 3-continued

| No. | Compound |
|---|---|
| III-46 | 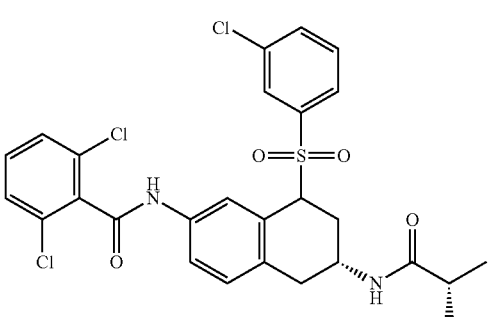 |

Methods for preparing compounds described herein are illustrated in the following synthetic schemes. The schemes are given for the purpose of illustrating the invention, but not for limiting the scope or spirit of the invention. Starting materials shown in the schemes can be obtained from commercial sources or be prepared based on procedures described in the literature.

The synthetic route illustrated in Scheme 1 is a general method for preparing various tetrahydronaphthalene compounds substituted at the 2-position with an amide and at the 8-position with an sulfonyl group. The synthetic route involves reaction of dihydronaphthalen-1(2H)-one A with nitric acid to provide 7-nitro-3,4-dihydronaphthalen-1(2H)-one B. Reduction of the ketone (such as with a hydride reagent) affords the alcohol C. Reaction of alcohol C with an activating agent (e.g., methanesulfonyl chloride) provides an activated intermediate that, upon addition of a thiol, affords the sulfide D. Reaction of sulfide D with an oxidizing agent (e.g., peroxybenzoic acid or hydrogen peroxide) affords sulphone E. The nitro group on sulfone E can be converted to an amino group using a dissolving metal reduction or hydrogenation reaction to provide amine compound F. Amide coupling of amine F with an acid (R'''CO$_2$H) in the presence of an amide coupling reagent (i.e., HATU or PyBop) provides desired tetrahydronaphthalene G. It is understood that an acid chloride (R'''C(O)Cl) can be used in lieu of the acid R'''CO$_2$H and amide coupling reagent in the step used to produce tetrahydronaphthalene G.

The reaction procedures in Scheme 1 are contemplated to be amenable to preparing a wide variety of substituted tetrahydronaphthalene compounds. For example, numerous substituted 3,4-dihydronaphthalen-1(2H)-one compounds are described in the literature and/or are commercially available. Furthermore, if a functional group on the molecule would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: N.Y., 1991, for further description of protecting chemistry and strategies. In certain other embodiments, a functional group in substituents R, R', and/or R'' in 5,6,7,8-tetrahydro-1,5-naphthryridine F can converted to another functional group using standard functional group manipulation procedures known in the art. See, for example, "Comprehensive Organic Synthesis" (B. M. Trost & I. Fleming, eds., 1991-1992.

SCHEME 1.

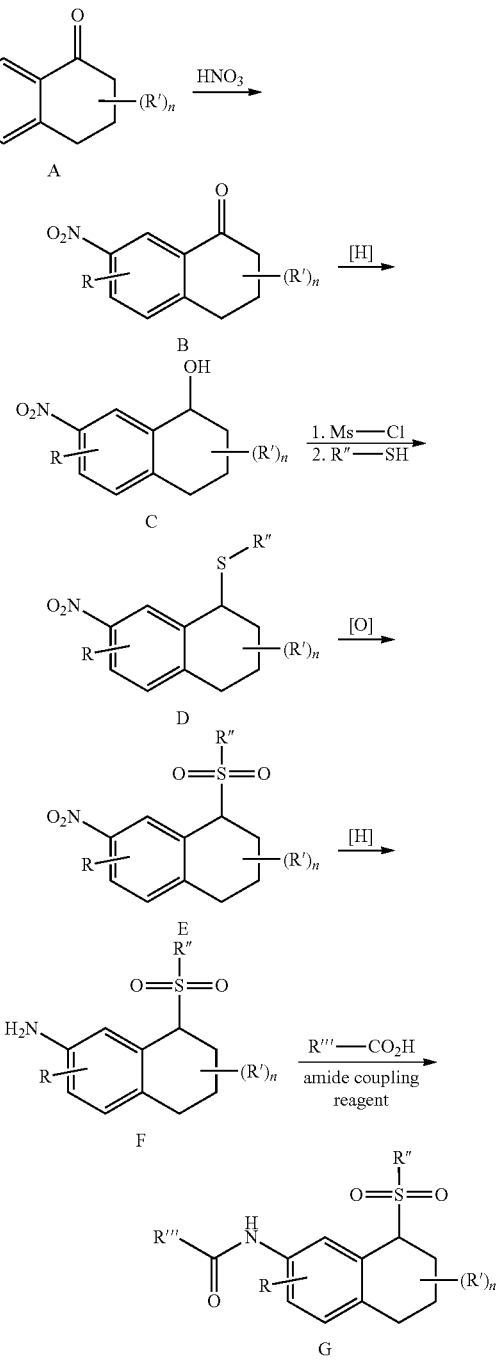

R and R' may be, for example, hydrogen or a substituent, such as methyl;
R'' may be, for example, a cyclic group, such as phenyl;
R''' is a carbon group, such as alkyl or aryl;
n is 0 or an integer, such as 1, 2, or 3.

In certain embodiments, compound A in Scheme 1 may have a chiral center on its bicyclic core. Exemplary chiral forms of compound A can be prepared based on procedures described in Schemes 2 and 3 below. Scheme 2 illustrates a general route to prepare chiral dihydronaphthalen-1(2H)-ones from a lactone. The synthetic route involves diastereoselective addition of a cuprate to unsaturated butyrolactone A-2, which is available in either enantiomeric form from L-glutamic acid, D-ribonolactone or D-mannitol. This diastereoselective addition provides a saturated lactone intermediate (not shown) that can be alkylated selectively to afford lactone B-2. For further description of related synthetic procedures, see, for example, Hanessian, S.; Murray, P. J. *J. Org. Chem.* 1987, 52, 1170-1172. If a second substituent is desired at the a-carbonyl position, lactone B-2 can be treated with a strong base (such as lithium diisopropylamide (LDA)), followed by addition of an alkyl halide to provide lactone C-2. For further description of related synthetic procedures, see, for example, Takano et al. in *J. Chem. Soc. Chem. Comm.* 1983, pages 760-762. The next steps involve opening the ring of lactone C-2, periodate oxidation, and reduction of the resultant intermediate aldehyde to provide lactone D-2. Then, the lactone D-2 is treated with trimethylsilyl iodide (TMSI) in the presence of an alcohol (e.g., methanol) to provide iodoester E-2. Then, iodoester E-2 is reacted with zinc to form an alkyl zinc reagent, which is exposed to haloaromatic compound F-2 in the presence of a palladium catalyst to provide carboxylic ester G-2. Reaction of carboxylic ester G-2 with a strong Lewis acid (e.g., AlCl$_3$, or BF$_3$·(OEt)$_2$) affords ketone H-2, which may be used in lieu of compound A in Scheme 1.

SCHEME 2.

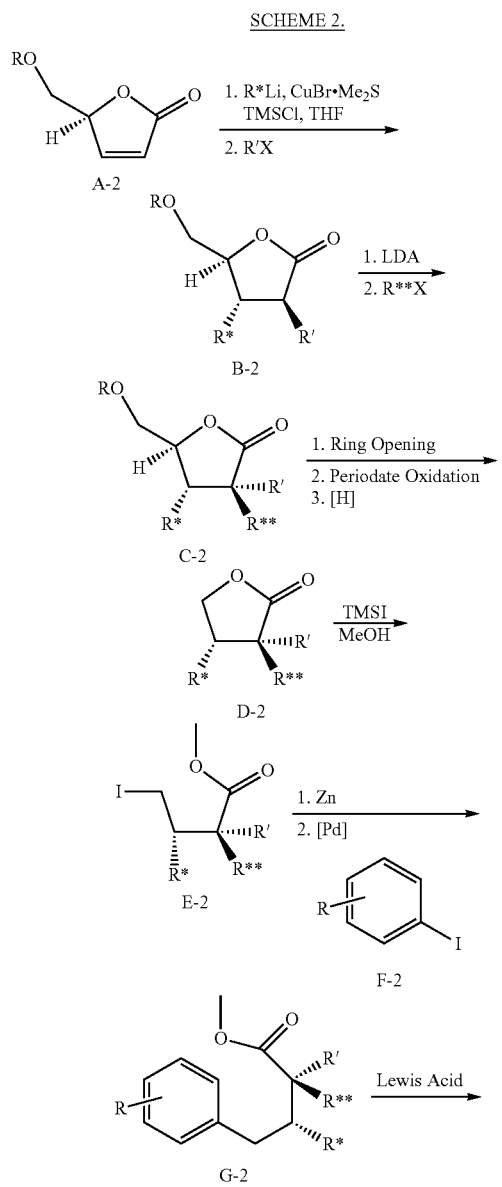

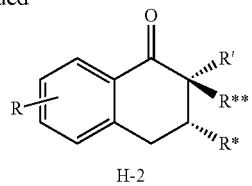

R may be, for example, hydrogen or a substituent, such as methyl; and R', R*, and R** are substituents, such as methyl.

Scheme 3 illustrates another general route to prepare chiral dihydronaphthalen-1(2H)-ones. This route involves diastereoselective addition of a benzylic copper reagent to acrylate A-3 containing a chiral auxillary (Qn) to afford compound C-3. For further description of related synthetic procedures, see, for example, van Heerden et al. in *Tet. Lett.* 1997, 38, 1821-24. Alternatively, a cuprate reagent can be added to substituted 4-phenylbut-2-enoic acid B-3 to afford compound C-3. The chiral auxiallary can be utilized to direct enantioselective alkylation of a suitable electrophile (R'X, where X is, for example, a halide or mesylate) to afford compound D-3. Treatment of compound D-3 with a Lewis acid to promote a Friedel Crafts like-reaction provides chiral dihydronaphthalen-1(2H)-one E-3.

SCHEME 3.

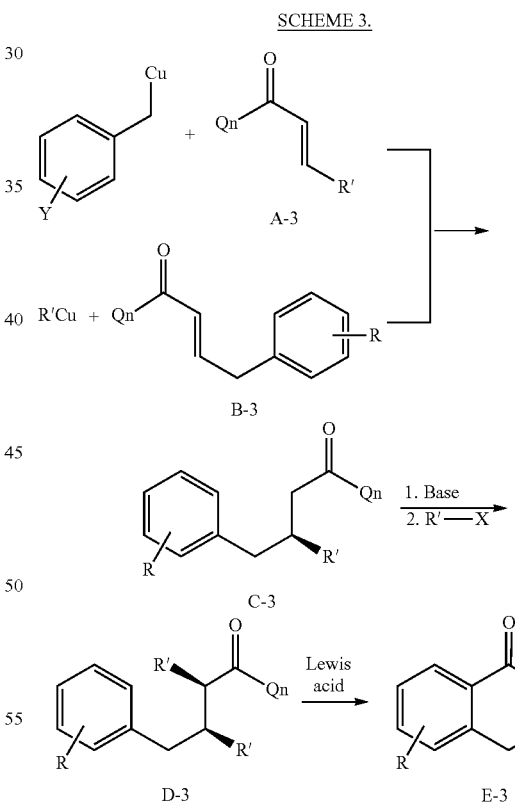

R and R' substituents, such as methyl.

Scheme 4 illustrates a general route for providing chromane compounds having an amide group at the 6-position and a sulfonyl group at the 4-position. The synthetic route involves cyclocondensation of an aldehyde with 4-nitro-2-acyl-phenol A-4 to provide chromanone B-4. Reduction of the ketone using, for example, a hydride, affords alcohol C-4.

Reaction of alcohol C-4 with an activating agent (e.g., methanesulfonyl chloride) provides an activated intermediate that, upon addition of a thiol, affords sulfide D-4. Reaction of sulfide D-4 with an oxidizing agent (e.g., peroxybenzoic acid or hydrogen peroxide) affords sulphone E-4. The nitro group on sulfone E-4 can be converted to an amino group using a dissolving metal reduction or hydrogenation reaction to provide amine compound F-4. Amide coupling of amine F-4 with an acid (R'''CO₂H) in the presence of an amide coupling reagent (i.e., HATU or PyBop) provides desired tetrahydronaphthalene G-4. It is understood that an acid chloride (R'''C(O)Cl) can be used in lieu of acid R'''CO₂H and amide coupling reagent in the step used to produce tetrahydronaphthalene G-4.

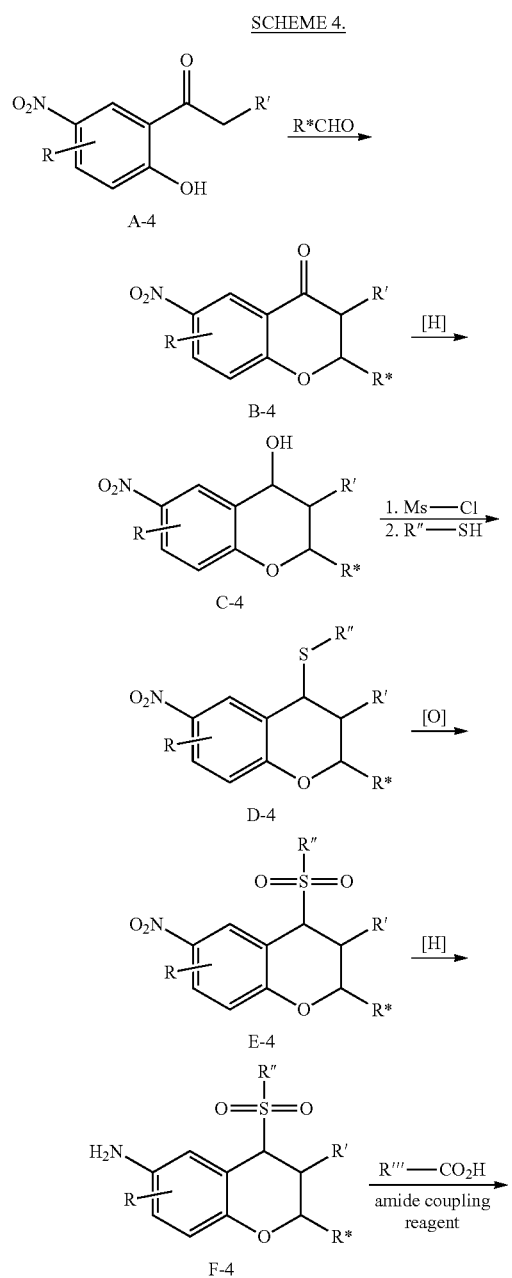

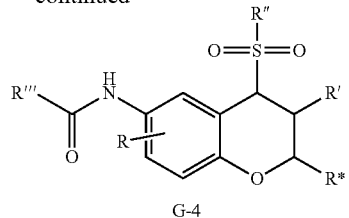

R, R', R*, and R** may be substituents, such as methyl;
R'' may be, for example, a cyclic group, such as phenyl
R''' is an carbon group, such as alkyl or aryl.

II. Therapeutic Applications of Bicyclic Sulfone Compounds

It is contemplated that the bicyclic sulfone compounds described herein, such as a compound of Formula I, II, III, or IV, provide therapeutic benefits to subjects suffering from an immune disorder or inflammatory disorder. Accordingly, one aspect of the invention provides a method of treating a disorder selected from the group consisting of an immune disorder or inflammatory disorder. The method comprises administering a therapeutically effective amount of a bicyclic sulfone compound described herein, such as a compound of Formula I, II, III, or IV, to a subject in need thereof to ameliorate a symptom of the disorder, wherein Formulae I-IV are as described above. In certain embodiments, the particular compound of Formulae I-IV is a compound defined by one of the embodiments described above.

In certain embodiments, the disorder is an immune disorder. In certain other embodiments, the disorder is an inflammatory disorder. In certain other embodiments, the disorder is an autoimmune disorder. In certain other embodiments, the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

In certain other embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, or an immune disorder associated with or arising from activity of pathogenic lymphocytes. In certain embodiments, the psoriasis is plaque psoriasis, guttate psoriasis, inverse psoriasis, pustular psoriasis, or erythrodermic psoriasis.

In certain other embodiments, the disorder is rheumatoid arthritis.

In certain embodiments, the subject is a human. In certain embodiments, the compound is a compound of Formula II or III.

Another aspect of the invention provides for the use of a compound described herein (such as a compound of Formula I, II, III, or IV) in the manufacture of a medicament. In certain embodiments, the medicament is for treating a disorder described herein, such as rheumatoid arthritis.

Another aspect of the invention provides for the use of a compound described herein (such as a compound of Formula I, II, III, or IV) for treating a medical disorder, such a medical disorder described herein (e.g., rheumatoid arthritis).

Further, it is contemplated that bicyclic sulfone compounds described herein, such as a compound of Formula I, II, III, or IV, can inhibit the activity of RORγ. Accordingly, another aspect of the invention provides a method of inhibiting the activity of RORγ. The method comprises exposing a RORγ to an effective amount of a bicyclic sulfone compound described herein, such as a compound of Formula I, II, III, or IV, to inhibit said RORγ, wherein Formula I, II, III, and IV are as described above. In certain embodiments, the particular compound of Formula I, II, III, or IV is a compound defined by one of the embodiments described above.

Further, it is contemplated that bicyclic sulfone compounds described herein, such as a compound of Formula I, II, III, or IV, can reduce the amount of interleukin-17 (IL-17) in a subject. IL-17 is a cytokine that affects numerous biological functions, including inducing and mediating pro-inflammatory responses. Accordingly, another aspect of the invention provides a method of reducing the amount of IL-17 in a subject. The method comprises administering to a subject an effective amount of a bicyclic sulfone compound described herein, such as a compound of I, II, III, or IV, to reduce the amount of IL-17 in the subject, wherein Formula I, II, III, and IV are as described above. In certain embodiments, the particular compound of Formula I, II, III, or IV is a compound defined by one of the embodiments described above.

In certain embodiments, the subject is a human. In certain embodiments, administering the compound reduces the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that bicyclic sulfone compounds described herein, such as a compound of Formula I, II, III, or IV, may inhibit the synthesis of IL-17 in a subject. Accordingly, another aspect of the invention provides a method of inhibiting the synthesis of IL-17 in a subject. The method comprises administering to a subject an effective amount of a compound described herein, e.g., a compound of Formula I, II, III, or IV, to inhibit the synthesis of IL-17 in the subject, wherein Formula I, II, III, and IV are as described above. In certain embodiments, the particular compound of Formula I, II, III, or IV is a compound defined by one of the embodiments described above. In certain embodiments, the bicyclic sulfone compound is a compound of Formula II or III.

The description above describes multiple embodiments providing definitions for variables used herein. The application specifically contemplates all combinations of such variables, e.g., particular combinations of the definitions set forth for variables A and X.

Compounds can be tested for inhibition of ROR using procedures described in the literature. Exemplary procedures for testing a compound for ability to inhibit RORγ activity include (i) a RORγ-Ligand Binding Domain (LBD) TR-FRET Assay, and (ii) a RORγ Reporter Assay. The RORγ-Ligand Binding Domain (LBD) TR-FRET Assay is described in Example 3 herein. The RORγ Reporter Assay is described below:

General Procedures for RORγReporter Assay

Inhibition of RORγt in cells is determined using a reporter system in HEK293 cells employing a luciferase readout. The RORγt DNA binding domain (DBD) is replaced with heterologous yeast GAL4 DBD using standard recombinant DNA methods. The resulting GAL4-RORγt-LBD fusion construct is placed under the control of a constitutive cytomegalovirus (CMV) promoter by cloning it into the CMV-driven mammalian expression vector pCDNA3.1+– (Promega Corporation, Madison, Wis.).

A transcriptional reporter expression construct is used to monitor GAL4-RORγ activity, which contains five copies of the GAL4 binding sequence (UAS) controlling expression of a firefly luciferase reporter gene. This construct, pGL4.31, is commercially available from Promega Corporation, Madison Wis. Both constructs are transfected in bulk into HEK-293 cells using standard lipid-based transfection techniques, which allows the GAL4-RORγ-LBD fusion protein to drive expression of the luciferase reporter. Control transfections are performed with an empty pCDN3.1+ vector.

The next day, cells are plated into 384 well plates, test compounds are added, and the plates are incubated overnight. Test compounds capable of blocking the GAL4-RORg fusion protein from initiating expression of the luciferase signal are identified. Promega firefly assays kits are used to stabilize the luciferase signal, and the intensity of the luciferase signal is measured using an EnVision Multilabel Plate Reader (Perkin Elmer, Waltham, Mass.).

Detailed Description of the HEK293 Gal4 Reporter Assay

HEK 293 cells are transfected with GAL4-RORγτ-LBD construct (pcDNA3.1neo) and the pGL4.31 GAL4-luciferase reporter construct (Promega). For a background control, use empty pcDNA3.1neo and pGL4.31. Transfection protocol is for a single T75 flask performed with Mirus Trans-It 293 reagent. A 60 µL aliquot of Trans-IT reagent at room temperature is added drop wise to 1.5 mL of Optimem (Invitrogen). The resulting solution is mixed by inversion and incubated for 5-20 minutes at room temperature. This reagent mixture is added to 10 µg of DNA (5 µg of each expression vector). The solution is mixed by inversion and incubated at room temperature for 20 minutes.

While the Trans-IT reagent and DNA are incubating, harvest HEK-293 cells. Remove media from flasks via aspiration and add enough TrypLE Express (stable Trypsin-like reagent, Invitrogen) to cover the bottom of the flask. The mixture is incubated at room temperature until the cells are visibly loose in the flask (approximately 2-5 minutes). Add an equal volume of complete growth media, and then pipette to achieve a single cell suspension. Spin down $1 \times 10^7$ cells and re-suspend the cells in 10 mL of complete growth media (DMEM high glucose/10% dialyzed FBS/pen/strep; Invitrogen). The cells and transfection mixture are added to one T75 flask. The contents of the T75 flask are mixed and incubated overnight at 37° C. and 5% $CO_2$.

After 16-24 hours, cells are harvested and plated for test compound screening. Cells may be harvested as described above. Next, cells are counted and an appropriate number of cells are spun down. Then, cells are aspirated and re-suspended in complete growth media at a concentration of 0.5×

$10^6$ cells/mL. Plate 20 µL of the cell suspension into a white, tissue-culture treated 384 well plate. (10,000-20,000 cells/well).

A 10 mM stock solution of test compound in dimethylsulfoxide (DMSO) is diluted to 500× the final test concentration in DMSO, then diluted to 5× the final test concentration with complete growth medium to provide the Test Compound Solution. The concentration of DMSO in the Test Compound Solution is 0.2%. A 5 µL aliquot of Test Compound Solution is added to each test well in the 384 well plate previously plated with the cell suspension. Next, plates are spun briefly and incubated overnight at 37° C. and 5% $CO_2$.

After 16-24 hours, the luciferase assay is performed. Plates and luciferase reagent (e.g. One-Glo® or Dual Glo®; Promega, Madison, Wis.) are brought to room temperature. Next, a 25 µL aliquot of luciferase reagent is added to each well. Plates are spun down briefly and incubated at room temperature for 10 minutes. The luciferase signal is measured on an Envision plate reader (Perkin Elmer) set to the ultra sensitive luminescence setting.

$EC_{50}$ values for test compounds are calculated from the luciferase signal data using GraphPad Prism software.

III. Combination Therapy

Another aspect of the invention provides for combination therapy. Bicyclic sulfone compounds (e.g., a compound of Formula I, II, III, or IV) or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (ariflo) or roflumilast; (8) an antihistamine HI receptor antagonist; (9) an α1- and α2-adrenoceptor agonist; (10) an anticholinergic agent; (11) a β-adrenoceptor agonist; (12) an insulin-like growth factor type I (IGF-1) mimetic; (13) a glucocorticosoid; (14) a kinase inhibitor such as an inhibitor of a Janus Kinase (e.g., JAK 1 and/or JAK2 and/or JAK 3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab, and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

The amount bicyclic sulfone compound (e.g., a compound of Formula I, II, III, or IV) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a bicyclic sulfone compound (e.g., a compound of any one of formulae I, II, III, or IV) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the bicyclic sulfone compound (e.g., a compound of any one of formulae I, II, III, or IV) and the additional therapeutic agent(s) are administered in doses commonly employed when such agents are used as monotherapy for treating the disorder. In other embodiments, the bicyclic sulphone compound (e.g., a compound of any one of formulae I, II, III, or IV) and the additional therapeutic agent(s) are administered in doses lower than the doses commonly employed when such agents are used as monotherapy for treating the disorder. In certain embodiments, the bicyclic sulphone compound (e.g., a compound of any one of formulae I, II, III, or IV) and the additional therapeutic agent(s) are present in the same composition, which is suitable for oral administration.

In certain embodiments, the bicyclic sulfone compound (e.g., a compound of any one of formulae I, II, III, or IV) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the bicyclic sulfone compound (e.g., a compound of any one of formulae I, II, III, or IV), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preserving agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a bicyclic sulfone compound described herein (such as a compound of any one of Formulae I-IV or a specific compound described herein, such as in Tables 1-4) in a therapeutically effective amount for the treatment of an immune or inflammatory disorder, such as one of the particular immune disorders or inflammatory disorders described herein.

EXAMPLES

The invention now being generally described, will be more readily understood by reference to the following examples, which are included merely for purposes of illustration of certain aspects and embodiments of the present invention, and are not intended to limit the invention.

Example 1

Synthesis of 2-Chloro-6-fluoro-N-[8-(4-trifluoromethylbenzenesulfonyl)-5,6,7,8-tetrahydronaphthalen-2-yl]benzamide (1)

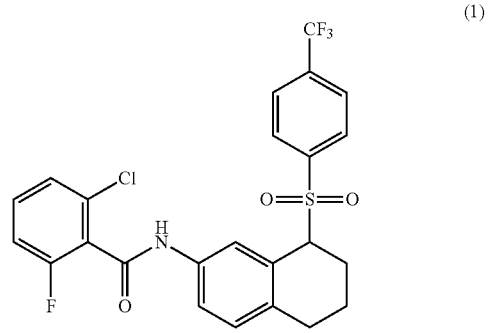 [SMILES: O=C(Nc1ccc2c(c1)C(S(=O)(=O)c1ccc(C(F)(F)F)cc1)CCC2)c1c(F)cccc1Cl]

The title compound was prepared according to the procedures described in Parts I-VI below.

Part I—Synthesis of 7-Nitro-1,2,3,4-tetrahydronaphthalen-1-ol

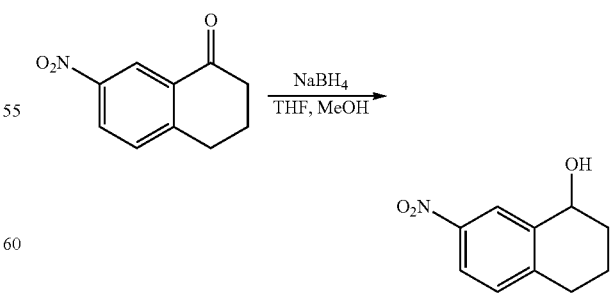

7-Nitro-3,4-dihydro-2H-naphthalen-1-one (2.0 g, 10 mmol) was dissolved in THF (50 mL) and NaBH$_4$ (0.95 g, 25 mmol) was added. MeOH (50 mL) was then added dropwise over 5 minutes and the reaction mixture was stirred for one hour. Saturated ammonium chloride was then added to the reaction mixture, and the resulting mixture was extracted three times with ethyl acetate. The organic solutions were combined and washed with brine, dried (Na$_2$SO$_4$) and concentrated to give 7-nitro-1,2,3,4-tetrahydronaphthalen-1-ol. Yield 1.83 g (95%). LCMS (ESI): calc. C$_{10}$H$_{11}$NO$_3$=193; obs. M+H=194.

Part II—Synthesis of Methanesulfonic acid 7-nitro-1,2,3,4-tetrahydronaphthalen-1-yl ester

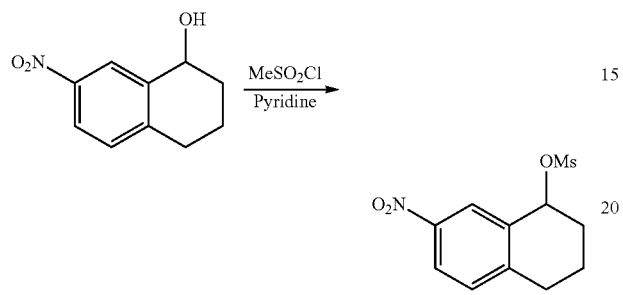

7-Nitro-1,2,3,4-tetrahydronaphthalen-1-ol (1.0 g, 5.2 mmol) was dissolved in a mixture of DCM (10 mL) and pyridine (10 mL). Then, the reaction mixture was cooled to 0° C. and methane sulphonyl chloride (0.44 mL, 5.7 mmol) was added dropwise, and the reaction mixture was stirred at 60° C. for 2 hours. Next, the reaction mixture was cooled to room temperature and then diluted with ethyl acetate, and washed with 1N HCl, saturated NaHCO$_3$, and brine. The organic solution was dried (Na$_2$SO$_4$) and concentrated to give methanesulfonic acid 7-nitro-1,2,3,4-tetrahydronaphthalen-1-yl ester. Yield 1.34 g (95%). LCMS (ESI): calc. C$_{11}$H$_{13}$NO$_5$S=271; obs. low ionization.

Part III—Synthesis of 7-Nitro-1-(4-trifluoromethylphenylsulfanyl)-1,2,3,4-tetra-hydronaphthalene

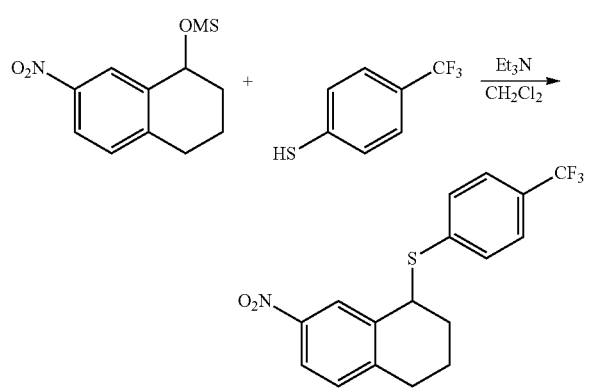

Methanesulfonic acid 7-nitro-1,2,3,4-tetrahydronaphthalen-1-yl ester (1.3 g, 4.8 mmol), was dissolved in a solution of triethylamine (3.35 mL, 24 mmol) and dichloromethane (10 mL). 4-Trifluoromethylbenzenethiol (1.7 g, 9.6 mmol) was then added and the reaction mixture was stirred at room temperature for 6 hours. Next, the reaction mixture was diluted with ethyl acetate and washed with 1N HCl, saturated sodium bicarbonate, and brine. The organic solution was dried (Na$_2$SO$_4$), concentrated, and purified by column chromatography (EtOAc/hexanes) to give 7-nitro-1-(4-trifluoromethylphenylsulfanyl)-1,2,3,4-tetrahydronaphthalene. Yield 1.45 g (86%). LCMS (ESI): calc. C$_{17}$H$_{14}$F$_3$NO$_2$S=353; obs. low ionization.

Part IV—Synthesis of 7-Nitro-1-(4-trifluoromethylbenzenesulfonyl)-1,2,3,4-tetra-hydronaphthalene

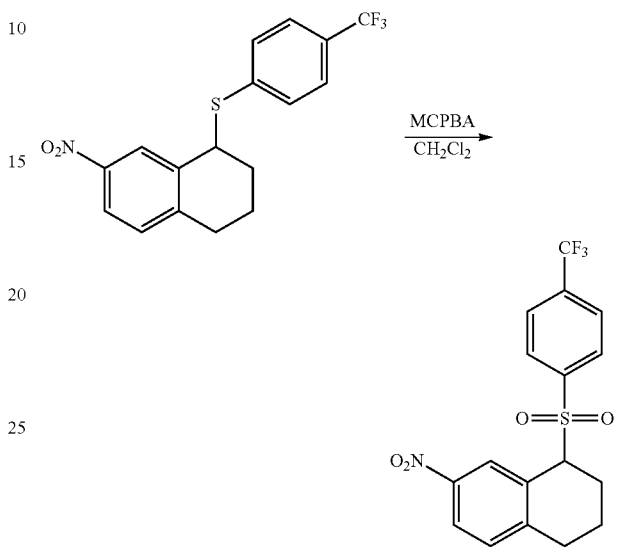

7-Nitro-1-(4-trifluoromethylphenylsulfanyl)-1,2,3,4-tetrahydronaphthalene (0.477 g, 1.3 mmol) was dissolved in dichloromethane (20 mL) and meta-chloro-perbenzoic acid (70%, 0.73 g, 3.0 mmol) was added. Next, the reaction mixture was stirred for 12 hours. Then, the reaction mixture was diluted with ethyl acetate and washed three times with 0.1N Na$_2$S$_2$O$_3$, washed three times with 0.1 N NaOH, once with water, and then with brine. The organic solution was dried (Na$_2$SO$_4$), concentrated, and purified by column chromatography (EtOAc/hexanes) to give 7-nitro-1-(4-trifluoromethylbenzenesulfonyl)-1,2,3,4-tetrahydro-naphthalene. Yield 0.314 g (63%). $^1$H NMR 250 MHz CDCl$_3$ δ 8.13 (dd, J=8.6, 2.4 Hz, 1H), 7.99 (d, J=2.4 Hz, 1H), 7.91 (A of ABq, J=8.6 Hz, 2H), 7.84 (B of ABq, J=8.6 Hz, 2H), 7.34 (d, J=8.6 Hz, 1H), 4.46 (dd, J=6.6, 3.5 Hz, 1H), 2.70-3.00 (m, 2H), 2.55-2.40 (m, 1H), 2.38-2.18 (m, 1H), 2.18-1.99 (m, 1H), 1.85-1.67 (m, 1H). LCMS (ESI): calc. C$_{17}$H$_{14}$F$_3$NO$_4$S=385; obs. low ionization.

Part V—Synthesis of 8-(4-Trifluoromethylbenzenesulfonyl)-5,6,7,8-tetrahydronaphthalen-2-yl amine

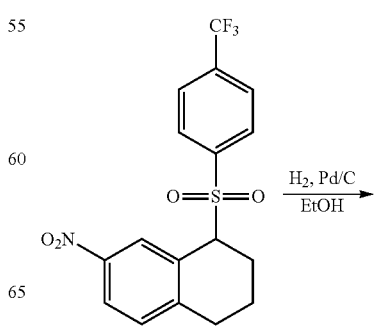

-continued

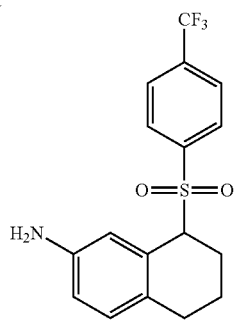

7-Nitro-1-(4-trifluoromethylbenzenesulfonyl)-1,2,3,4-tetrahydronaphthalene (0.314 g, 0.816 mmol) was dissolved in ethanol (20 mL) and 10% Pd/C (50 mg) was added. Then, the reaction mixture was agitated under a hydrogen atmosphere (60 p.s.i.) for one hour using a Parr shaker. Next, the reaction mixture was filtered through Celite and concentrated to give 8-(4-trifluoromethylbenzenesulfonyl)-5,6,7,8-tetrahydronaphthalen-2-ylamine. Yield 0.30 g crude. LCMS (ESI): calc. $C_{17}H_{16}F_3NO_2S=355$; obs. M+H=356.

Part VI—Synthesis of 2-Chloro-6-fluoro-N-[8-(4-trifluoromethylbenzenesulfonyl)-5,6,7,8-tetrahydronaphthalen-2-yl]benzamide

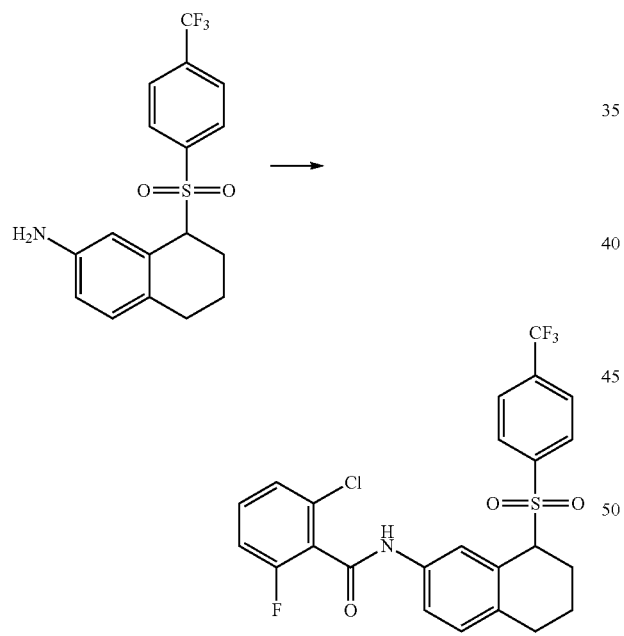

8-(4-Trifluoromethylbenzenesulfonyl)-5,6,7,8-tetrahydronaphthalen-2-ylamine (25 mg, 0.070 mmol) and diisopropylethylamine (23 μL, 0.14 mmol) were combined in dichloromethane (500 μL) to form a reaction mixture. 2-Chloro-6-fluorobenzoyl chloride (21 mg, 0.11 mmol) was then added and the reaction mixture, and the reaction mixture was stirred for 12 hours at room temperature. Next, methanol (100 μL) was added and the solvent was removed under reduced pressure to provide a residue, which was purified by HPLC to provide the title compound. LCMS (ESI): calc. $C_{24}H_{18}ClF_4NO_3S=511$; obs. M+H=512.

Example 2

Preparation of Additional Bicyclic Sulfone Compounds

The compounds in Table 4 below were prepared based on the experimental procedures described in Example 1 and in the detailed description. Starting materials can be obtained from commercial sources or readily prepared from commercially available materials.

TABLE 4

| Compound No. | Chemical Structure | LCMS (ESI): Calculated m/z | LCMS (ESI): Observed m/z |
|---|---|---|---|
| IV-1 | 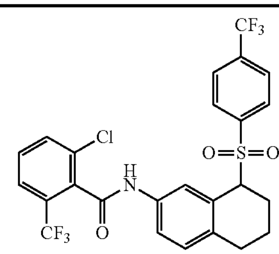 | 561 | M + H = 562 |
| IV-2 | 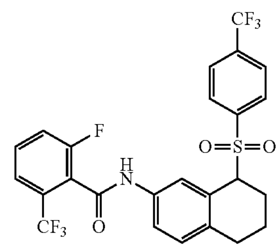 [SMILES: O=C(Nc1ccc2c(c1)C(S(=O)(=O)c1ccc(C(F)(F)F)cc1)CCC2)c1c(F)cccc1C(F)(F)F] | 545 | M + H = 546 |
| IV-3 | 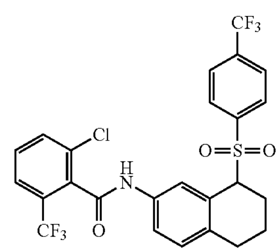 [SMILES: O=C(Nc1ccc2c(c1)C(S(=O)(=O)c1ccc(C(F)(F)F)cc1)CCC2)c1c(Cl)cccc1C(F)(F)F] | 527 | M + H = 528 |
| IV-4 | 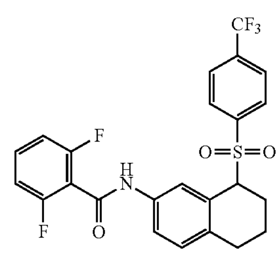 [SMILES: O=C(Nc1ccc2c(c1)C(S(=O)(=O)c1ccc(C(F)(F)F)cc1)CCC2)c1c(F)cccc1F] | 495 | M + H = 496 |

Example 3

Biological Assays for Inhibition of RORγ

Compounds from Examples 1 and 2 were tested for ability to inhibit RORγ activity using a RORγ-Ligand Binding Domain (LBD) TR-FRET Assay. Assay procedures and results are described below.

Part I—Procedures for RORγ-Ligand Binding Domain TR-FRET Assay

Recombinant, HIS-tagged RORγ-LBD was expressed in SF9 cells using a baculovirus expression system. Cells were lysed and the lysate was used as a source for RORγ-LBD for the assay. A 1:80 dilution of RORγ-LBD lysate in assay buffer (25 mM HEPES pH 7.0, 100 mM NaCl, 0.01% Tween, 0.1% BSA) was prepared and 5 µL was added to each well (RORγ-LBD final concentration ~3 nM). Control wells received lysate from SF9 cells not expressing RORγ-LBD.

Compounds to be tested were diluted to 100× final test concentration in DMSO and further diluted to 4× final test concentration using assay buffer to provide the test compound mixture. An aliquot (5 µL) of the test compound mixture was added to each well.

A 4× stock of biotinylated-LXXLL peptide from SRC1-2 (Biotin-CPSSHSSLTERHKILHRLLQEGSPS) was prepared in assay buffer and a 5 µL aliquot added to each well (450 nM final concentration). A 4× solution of europium tagged anti-HIS antibody (2 nM final concentration) and APC conjugated streptavidin (60 nM final concentration) were prepared and a 5 µL aliquot added to each well.

The final assay mixture was incubated for 4 hours to overnight, and the fluorescence signal was measured on an Envision plate reader: (Excitation filter=340 nm; APC emission=665 nm; Europium emission=615 nm; dichroic mirror=D400/D630; delay time=100 µs, integration time=200 µs).

$EC_{50}$ values for test compounds were calculated from the quotient of the fluorescence signal at 665 nm divided by the fluorescence signal at 615 nm using GraphPad Prism software

Part II—Results

Compounds 1, IV-1, IV-2, IV-3, and IV-4 from Examples 1 and 2 were tested and each compound was determined to have an $EC_{50}$ less than 150 nM in the RORγ-Ligand Binding Domain TR-FRET Assay.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:
1. A compound represented by Formula I:

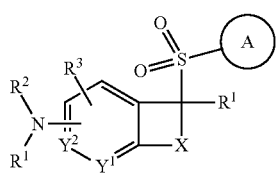

(I)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p$$C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$-[C($R^6$)($R^7$)]-[C($R^6$)$_2$]$_m$-ψ, —C(O)—[C($R^6$)($R^7$)]-[C($R^6$)$_2$]$_m$-ψ, or —C($R^6$)$_2$—N($R^8$)—[C($R^6$)($R^7$)]-[C($R^6$)$_2$]$_m$-ψ; wherein ψ is a bond to the ring carbon atom bearing the sulfonyl in Formula I;

$Y^1$ and $Y^2$ are each independently C($R^3$) or N;

$R^1$ represents independently for each occurrence hydrogen or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl; and m and p each represent independently for each occurrence 0, 1, or 2.

2. The compound of claim 1, wherein A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

3. The compound of claim 1, wherein A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

4. The compound of claim 1, wherein A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

5. The compound of claim 1, wherein X is —O-[C(R$^6$)(R$^7$)]-[C(R$^6$)$_2$]$_m$-ψ.

6. The compound of claim 1, wherein X is —C(R$^6$)$_2$-[C(R$^6$)(R$^7$)]-[C(R$^6$)$_2$]$_m$-ψ.

7. The compound of claim 1, wherein X is —C(O)—[C(R$^6$)(R$^7$)]-[C(R$^6$)$_2$]$_m$-ψ.

8. The compound of claim 1, wherein Y$^1$ and Y$^2$ are C(R$^3$).

9. The compound of claim 1, wherein at least one of Y$^1$ and Y$^2$ is N.

10. The compound of claim 1, wherein R$^1$ is hydrogen.

11. The compound of claim 1, wherein R$^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl.

12. The compound of claim 1, wherein R$^2$ is —C(O)—phenyl or —C(O)-benzyl; each of which is optionally substituted with 1, 2, or 3 substituents independently selected from the group consisting of halogen, $C_{1-6}$alkyl, and $C_{1-6}$haloalkyl.

13. The compound of claim 1, wherein R$^2$ is represented by:

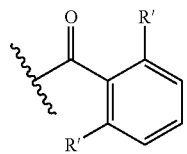

wherein each R' is independently halogen, $C_{1-6}$alkyl, or $C_{1-6}$haloalkyl.

14. The compound of claim 1, wherein R$^2$ is represented by:

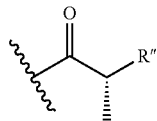

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—$C_{1-6}$alkyl, —C(O)—$C_{1-6}$alkyl, —C(O)N(R$^4$)(R$^5$), —S(O)$_p$$C_{1-6}$alkyl, —SO$_2$N(R$^4$)(R$^5$), and —N(R$^4$)SO$_2$($C_{1-6}$alkyl).

15. The compound of claim 1, wherein R$^3$ is hydrogen.

16. The compound of claim 1, wherein R$^7$ is hydrogen.

17. The compound of claim 1, wherein R$^7$ is hydroxyl, $C_{1-6}$hydroxyalkyl, $C_{1-6}$alkyl, $C_{1-6}$haloalkyl, —CO$_2$R$^6$, $C_{1-6}$alkylene-CO$_2$R$^6$, $C_{1-6}$ hydroxyalkylene-CO$_2$R$^6$, —N(R$^4$)(R$^5$), $C_{1-6}$alkylene-N(R$^4$)(R$^5$), $C_{1-6}$hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—$C_{1-6}$alkyl, or —N(R$^4$)C(O)R$^9$.

18. The compound of claim 1, wherein R$^7$ is $C_{1-6}$ hydroxyalkyl, $C_{1-6}$alkyl, $C_{1-6}$alkylene-CO$_2$R$^6$, —N(R$^4$)(R$^5$), $C_{1-6}$alkylene-N(R$^4$)(R$^5$), or $C_{1-6}$ alkylene-N(R$^4$)C(O)R$^9$.

19. The compound of claim 1, wherein R$^7$ is $C_{1-3}$ hydroxyalkyl, methyl, ethyl, or $C_{1-3}$alkylene-N(H)C(O)—$C_{1-4}$alkyl.

20. The compound of claim 1, wherein the compound is represented by Formula II:

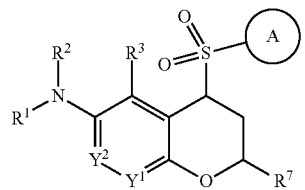

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —$C_{1-4}$alkylene-$C_{1-4}$alkoxy, and —$C_{1-4}$alkylene-N(R$^4$)(R$^5$);

Y$^1$ and Y$^2$ are each independently C(R$^3$) or N;

R$^1$ is hydrogen or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_n$-heterocyclyl, —C(O)—$C_{1-8}$alkyl, —C(O)—$C_{1-6}$alkylene-$C_{1-6}$ alkoxyl, —C(O)—$C_{1-6}$alkylene-cycloalkyl, or —C(O)—$C_{1-6}$ alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—$C_{1-6}$alkyl, —C(O)—$C_{1-6}$alkyl, —C(O)N(R$^4$)(R$^5$), —S(O)$_p$$C_{1-6}$alkyl, —SO$_2$N(R$^4$)(R$^5$), and —N(R$^4$)SO$_2$($C_{1-6}$alkyl);

R$^3$ represents independently for each occurrence hydrogen, halogen, or $C_{1-6}$alkyl;

R$^4$ and R$^5$ each represent independently for each occurrence hydrogen or $C_{1-6}$alkyl; or R$^4$ and R$^5$ taken together with the nitrogen atom to which they are attached form a 3-7 membered heterocyclic ring;

R$^6$ represents independently for each occurrence hydrogen or $C_{1-6}$alkyl;

R$^7$ is hydrogen, hydroxyl, $C_{1-6}$hydroxyalkyl, $C_{1-6}$alkyl, $C_{1-6}$haloalkyl, —CO$_2$R$^6$, $C_{1-6}$ alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$ hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—$C_{1-6}$alkyl, or $C_{1-6}$alkylene-N(R$^4$)(C(O)N(R$^4$)(R$^5$); or R$^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R$^9$ is hydrogen, $C_{1-6}$alkyl, $C_{1-6}$hydroxyalkyl, $C_{1-6}$alkylene-N(R$^4$)(R$^5$), or $C_{1-6}$alkyl ene-N(R$^4$)C(O)—$C_{1-6}$ alkyl; and m and p each represent independently for each occurrence 0, 1, or 2.

21. The compound of claim 20, wherein A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

22. The compound of claim 20, wherein A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

23. The compound of claim 20, wherein $Y^1$ and $Y^2$ are $C(R^3)$.

24. The compound of claim 20, wherein at least one of $Y^1$ and $Y^2$ is N.

25. The compound of claim 20, wherein $R^1$ is hydrogen.

26. The compound of claim 20, wherein $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl.

27. The compound of claim 20, wherein $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl.

28. The compound of claim 20, wherein $R^2$ is represented by:

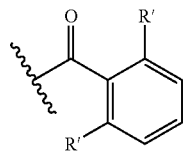

wherein each R' is independently halogen, $C_{1-6}$alkyl, or $C_{1-6}$haloalkyl.

29. The compound of claim 20, wherein $R^2$ is represented by:

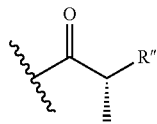

wherein R" is $C_{1-6}$alkyl, aryl, or heterocyclyl, each of which is optionally substituted with 1, 2, or 3 substituents independently selected from the group consisting of halogen, hydroxyl, $C_{1-6}$ alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl).

30. The compound of claim 20, wherein $R^3$ is hydrogen.

31. The compound of claim 20, wherein $R^7$ is hydrogen.

32. The compound of claim 20, wherein $R^7$ is $C_{1-6}$hydroxyalkyl, $C_{1-6}$alkyl, $C_{1-6}$alkylene-CO$_2$R$^6$, $C_{1-6}$alkylene-N(R$^4$)(R$^5$), or $C_{1-6}$alkylene-N(R$^4$)C(O)R$^9$.

33. The compound of claim 1, wherein the compound is represented by Formula III:

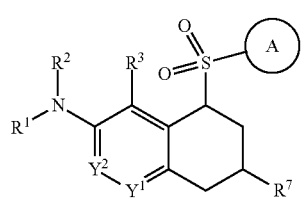

(III)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, and —C$_{1-4}$alkylene-N(R$^4$)(R$^5$);

$Y^1$ and $Y^2$ are each independently $C(R^3)$ or N;

$R^1$ is hydrogen or $C_{1-6}$alkyl;

$R^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$ alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —CO$_2$R$^6$, $C_{1-6}$ alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$ hydroxyalkylene-N(R$^4$)(R$^5$), —N(R$^4$)C(O)R$^9$, $C_{1-6}$alkylene-N(R$^4$)C(O)R$^9$, $C_{1-6}$ alkylene-C(O)N(R$^4$)(R$^5$), —N(R$^4$)CO$_2$—C$_{1-6}$alkyl, or $C_{1-6}$alkylene-N(R$^4$)(C(O)N(R$^4$)(R$^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $C_{1-6}$alkylene-N(R$^4$)(R$^5$), or $C_{1-6}$ alkylene-N(R$^4$)C(O)—C$_{1-6}$ alkyl; and m and p each represent independently for each occurrence 0, 1, or 2.

34. The compound of claim 33, wherein A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

35. The compound of claim 33, wherein A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

36. The compound of claim 33, wherein $Y^1$ and $Y^2$ are $C(R^3)$.

37. The compound of claim 33, wherein at least one of $Y^1$ and $Y^2$ is N.

38. The compound of claim 33, wherein $R^1$ is hydrogen.

39. The compound of claim 33, wherein $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl.

40. The compound of claim 33, wherein $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl.

41. The compound of claim 33, wherein $R^2$ is represented by:

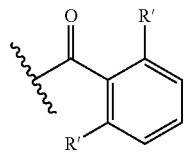

wherein each R' is independently halogen, $C_{1-6}$alkyl, or $C_{1-6}$haloalkyl.

42. The compound of claim 33, wherein $R^2$ is represented by:

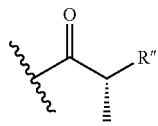

wherein R" is $C_{1-6}$alkyl, aryl, or heterocyclyl, each of which is optionally substituted with 1, 2, or 3 substituents independently selected from the group consisting of halogen, hydroxyl, $C_{1-6}$ alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl).

43. The compound of claim 33, wherein $R^3$ is hydrogen.

44. The compound of claim 33, wherein $R^7$ is hydrogen.

45. The compound of claim 33, wherein $R^7$ is $C_{1-6}$ hydroxyalkyl, $C_{1-6}$alkyl, $C_{1-6}$alkylene-$CO_2R^6$, —N($R^4$)($R^5$), $C_{1-6}$alkylene-N($R^4$)($R^5$), or $C_{1-6}$ alkylene-N($R^4$)C(O)$R^9$.

46. A compound in any one of Tables 1, 2, 3, or 4 herein or a pharmaceutically acceptable salt thereof.

47. A pharmaceutical composition comprising a compound of claim 1 and a pharmaceutically acceptable carrier.

48. A method of treating a disorder selected from the group consisting of an immune disorder and inflammatory disorder, comprising administering a therapeutically effective amount of a compound of claim 1 to a subject in need thereof to ameliorate a symptom of the disorder.

49. The method of claim 48, wherein the disorder is rheumatoid arthritis, psoriasis, chronic graft-versus-host disease, acute graft-versus-host disease, Crohn's disease, inflammatory bowel disease, multiple sclerosis, psoriasis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

50. The method of claim 48, wherein the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, or an immune disorder associated with or arising from activity of pathogenic lymphocytes.

51. The method of claim 48, wherein the disorder is rheumatoid arthritis.

52. The method of claim 48, wherein the subject is a human.

* * * * *